US006069173A

United States Patent [19]

Hainrihar

[11] Patent Number: 6,069,173

[45] Date of Patent: May 30, 2000

[54] SYNERGISTIC INSECTICIDAL COMPOSITIONS COMPRISING CAPSICUM AND SYNTHETIC SURFACTANT AND USE THEREOF

[75] Inventor: Gary C. Hainrihar, Lawton, Mich.

[73] Assignee: Kalamzoo Holdings, Inc., Kalamazoo, Mich.

[21] Appl. No.: 09/049,232

[22] Filed: Mar. 27, 1998

[51] Int. Cl.[7] .......................... A01N 33/02; A01N 25/00; B01J 13/00

[52] U.S. Cl. ............................ 514/627; 424/45; 424/405; 514/937; 514/942; 514/975; 516/24; 516/25; 516/30; 516/77

[58] Field of Search ................................. 516/24, 25, 30, 516/77; 424/405; 514/627, 975

[56] References Cited

U.S. PATENT DOCUMENTS

| | | | |
|---|---|---|---|
| 4,851,421 | 7/1989 | Iwasaki et al. | 424/405 X |
| 5,178,879 | 1/1993 | Adekunle et al. | 514/627 X |
| 5,206,021 | 4/1993 | Dookhith et al. | 424/405 |
| 5,318,960 | 6/1994 | Toppo | 514/975 X |
| 5,456,916 | 10/1995 | Kurata et al. | 514/627 X |
| 5,525,597 | 6/1996 | Hainrihar et al. | 514/627 X |
| 5,599,803 | 2/1997 | Hainrihar et al. | 514/627 X |
| 5,762,963 | 6/1998 | Byas-Smith | 514/627 X |

*Primary Examiner*—Richard D. Lovering
*Attorney, Agent, or Firm*—The Firm of Gordon W. Hueschen

[57] ABSTRACT

Insecticidal compositions comprising a synthetic surfactant and capsaicin or other capsaicinoid exhibit synergistic effects against numerous insects, not only as to activity-enhancement effect but more importantly as to activity-extending effect, especially against Fall Army Worms, Alfalfa Weevils, Corn Ear Worms, Corn Leaf Aphids, True Army Worms, Grasshoppers, Potato Leaf Hoppers, Beanleaf Beetles, and Soybean Thrips, when applied to the insect or its habitat, especially as an aqueous solution, suspension, or emulsion. Effective kill levels are observed as long as fourteen days after application whereas, using the individual components, effective kill levels do not ordinarily extend beyond 24 hours after application.

52 Claims, 14 Drawing Sheets

SYNERGISTIC INSECTICIDAL COMPOSITIONS COMPRISING CAPSICUM AND SYNTHETIC SURFACTANT AND USE THEREOF

BACKGROUND OF THE INVENTION

1. Field of the Invention

Insecticidal compositions comprising a synthetic surfactant and capsaicin or other capsaicinoid, especially in the form of mixtures of capsaicinoids derived from Capsicum species, and the insecticidal employment thereof. According to the present invention, the employment of a synthetic surfactant in combination with capsaicin or other capsaicinoids, especially in the form of mixtures of capsaicinoids, especially mixtures derived from Capsicum species, but also including synthetic capsaicinoids such as the vanillyl amide of pelargonic acid (N-(4-hydroxy-3-methoxybenzyl)nonamide), N-(4-hydroxy-3-methoxybenzyl) heptamide, N-(4-hydroxy-3-methoxybenzyl) octamide, N-(4-hydroxy-3-methoxybenzyl) decamide, N-(4-hydroxy-3-methoxybenzyl) undecamide, and N-(4-hydroxy-3-methoxybenzyl) dodecamide, produces synergistic effectiveness not only as to enhancement effect but more importantly as to extending or prolonging effect in combating numerous insects, especially Fall Army Worms, Alfalfa Weevils, Corn Ear Worms, Corn Leaf Aphids, True Army Worms, Grasshoppers, Potato Leaf Hoppers, Beanleaf Beetles, and Soybean Thrips. As used herein, the term "capsaicinoid" is broad enough to encompass capsaicin and structurally related compounds or mixtures thereof typically found in most Capsicum species, including *Capsicum annuum, Capsicum frutescens, Capsicum baccatum, Capsicum chinense* and *Capsicum pubescens.* The insecticidal activity of the compositions of the present invention has been established on weeds, grasses, corn, beans, garden vegetables, fruits, and flowers, inter alia, the habitat or environment of the insect not being of particular significance and certainly not a critical limitation since the insecticidal compositions of the present invention may be employed against insects wherever they may be found.

2. Prior Art

The closest prior art is set forth in my previous U.S. Pat. Nos. 5,525,597, issued Jun. 11, 1996 and 5,599,803 issued Feb. 4, 1997, directed respectively to combinations of an organophosphorous insecticidal ingredient and an activity-enhancing amount of a capsaicinoid in defined weight ratio limits and an effective insecticidal amount of a non-organophosphorous insecticidal ingredient plus an activity-enhancing amount of a capsaicinoid, also in defined weight ratio limits. These patents are submitted to be the closest prior art, although they do not in the slightest suggest a combination of a synthetic surfactant and a capsaicinoid, especially within the weight ratio limits hereinafter defined, for the purpose of producing a synergistic enhanced insecticidal effect and more importantly an extending or prolonging insecticidal effect of the compositions of the present invention to produce effective kill levels up to fourteen (14) days after application which, in most situations evaluated, was in fact found to be up to fourteen (14) times as long a period of effectiveness than produced by either of the two (2) ingredients alone or which could be calculated from the effectiveness of the individual components alone.

The prior art set forth in detail in our previous atents is considered to be related art but still fails, ust as do my previous patents, to show or suggest the presently-claimed combination of a synthetic surfactant and a capsaicinoid with all of its synergistic advantages of enhancement and prolongation of effective kill levels in actual field testing and use.

Although the compositions of my above-identified earlier patents are highly advantageous and effective in use, there is a constant effort to improve the environment and to employ insecticidal ingredients which are less toxic and in general safer so as to make them not only less hazardous to the user but also to make them more environmentally friendly and avoid the possibility of retention of toxic levels of ingredients on the habitat of the insects being eliminated and on the produce which is exposed to the treatment. The composition and method of the present invention go far in reaching these objectives since, although synthetic surfactants do not occur naturally, many are biodegradable and are certainly regarded as less toxic than many commonly used insecticides.

OBJECTS OF THE INVENTION

It is an object of the present invention to provide a new and improved insecticidal composition having enhanced activity when compared to the activity of the individual components thereof and moreover in the prolongation or extension of insecticidal effectiveness when compared to the individual components thereof, the said composition comprising a synthetic surfactant and capsaicin or mixture of capsaicinoids.

Another object of the invention is to provide a method of employing such insecticidal composition of enhanced and/or prolonged insecticidal activity for the elimination of insects which are damaging to growing plants and crops and a further object is the provision of such insecticidal composition which has enhanced effectiveness against Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips. Still a further object of the invention is the provision of such composition and method which are effective in use and actual field applications, and particularly when applied to the insect or its habitat in the form of an aqueous solution, suspension, or emulsion as a spray, including an aerosol spray, and suitable for application to large stands of crops in the form of an aerial spray by a crop-dusting type airplane.

Yet another object of the invention is the provision of such composition and method wherein the capsaicinoids are derived from plants of the Capsicum species, which in turn are preferably provided in the form of Capsyn®, as hereinafter more fully identified.

Still other objects will become apparent hereinafter and yet additional objects will be obvious to one skilled in the art to which this invention pertains.

SUMMARY OF THE INVENTION

What I believe to be my invention, then, inter alia, comprises the following, singly or in combination:

An insecticidal composition, having enhanced and/or prolonged insecticidal effectiveness when compared with the individual components when used alone, comprising as essential ingredient an effective amount of a combination of (A) at least one synthetic surfactant selected from the group consisting of phosphate esters of alkyl poly(ethyleneoxy) ethanols, phosphate esters of aryl alkyl poly(ethyleneoxy) ethanols, esters of fatty acids and polyethylene glycol, ethers of fatty alcohols and polyethylene glycol, dialkyl sodium or potassium sulfosuccinates, sodium or potassium naphthalene sulfonates, sodium or potassium alkyl naphthalene sulfonates, arylalkyl poly(ethyleneoxy) alcohols and ethers, alkyl sulfonates, and alkylarylsulfonates, plus (B) at least one capsaicinoid, the weight ratio of (B) to (A) being between about 1:2.5 and 1:400 and the amount of capsaicinoid to total insecticidal composition, including both active and inactive ingredients, being between about 50 and 2000 parts per million by weight; such a composition wherein the weight ratio of (B) to (A) is between about 1:10 and 1:200; such a composition wherein the weight ratio of (B) to (A) is approximately 1:25 to 1:50 and the amount of capsaicinoid to total insecticidal composition, including both active and inactive ingredients, is between about 100 and 400 parts per million by weight; such a composition wherein the capsaicinoid (B) comprises capsaicin; such a composition wherein the capsaicinoid (B) is in the form of an essentially lipid-free and optionally aqueous solution thereof in a polyol; such a composition wherein the capsaicinoid (B) is derived from a species of Capslcum; such a composition wherein the capsaicinoid (B) is one or more of capsaicin, norcapsaicin, dihydrocapsaicin, nordihydrocapsaicin, homodihydrocapsaicin, and homocapsaicin; such a composition wherein the capsaicinoid (B) is a synthetic capsaicinoid; such a composition wherein the capsaicinoid (B) comprises one or more of N-(4-hydroxy-3-methoxybenzyl) heptamide, N-(4-hydroxy-3-methoxybenzyl) octamide, N-(4-hydroxy-3-methoxybenzyl)nonamide, N-(4-hydroxy-3-methoxybenzyl) decamide, N-(4-hydroxy-3-methoxybenzyl) undecamide, and N-(4-hydroxy-3-methoxybenzyl) dodecamide; such a composition wherein the synthetic surfactant is a mixture of phosphate esters of alkylaryl poly(eyleneoxy) ethanols of the formula

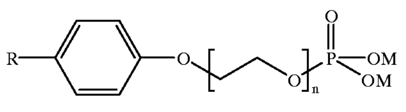

wherein $R=C_4H_9—C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

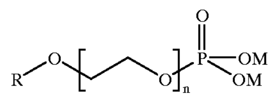

wherein $R=C_4H_9—C_{16}H_{33}$ alkyl, n=4–15,

M=H, Na, K, $NH_4$, $CH_3$, or $C_2H_5$; such a composition which also contains ammonium and sulfate ions; such a composition wherein the synthetic surfactant comprises dibutyl sodium or potassium sulfosuccinate; such a composition wherein the synthetic surfactant comprises di-2-ethylhexyl sodium or potassium sulfosuccinate; such a composition wherein the synthetic surfactant comprises the sodium or potassium salt of naphthalene sulfonic acid; such a composition wherein the synthetic surfactant comprises the sodium or potassium salt of diisopropyl naphthalene sulfonic acid; such a composition wherein the synthetic surfactant comprises a mixture of alkylaryl poly(ethyleneoxy) ethers of the formula

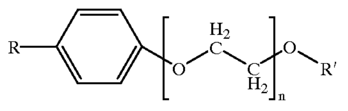

wherein $R=C_4H_9—C_{16}H_{33}$ alkyl, predominantly para oriented, n=4–15.

R'=H, $CH_3$, or $C_2H_5$.

Further, an insecticidal composition comprising a mixture of (A) at least one synthetic surfactant and (B) at least one capsaicinoid in a ratio between about 1:2.5 and 1:400 by weight, the concentration of the ingredients being an insecticidally-effective concentration, and the amount of capsaicinoid to total insecticidal composition, including both active and inactive ingredients, being between about 50 and 2000 parts per million by weight; such a composition in the form of a dilutable concentrate; such a concentrate wherein the composition is dilutable with water; such a composition wherein (B) is capsaicin or a mixture of capsaicinoids and (A) comprises a mixture of phosphate esters of alkylaryl poly(ethyleneoxy) ethanols of the formula

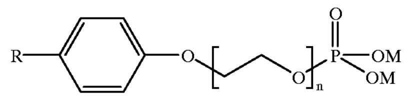

wherein $R=C_4H_9—C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

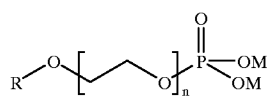

wherein $R=C_4H_9—C_{16}H_{33}$ alkyl, n=4–15,

M=H, Na, K, $NH_4$, $CH_3$, or $C_2H_5$; such a composition wherein the synthetic surfactant is selected from the group consisting of sulfosuccinates, naphthalene sulfonates, alkyl poly(ethyleneoxy) ethers, and alkylaryl poly(ethyleneoxy) ethanols.

Moreover, a method of killing insects comprising the step of spraying a combination of (A) at least one synthetic surfactant plus (B) at least one capsaicinoid, upon the insect or upon its habitat, the weight ratio of (B) to (A) being between about 1:2.5 and 1:400 and the amount of capsaicinoid to total insecticidal composition, including both active and inactive ingredients, being between about 50 and 2000 parts per million by weight; such a method wherein the capsaicinoid (B) is in the form of an essentially lipid-free and optionally aqueous solution thereof in a polyol; such a method for controlling insects comprising contacting insects or their habitat with such an insecticidally-effective composition; such a method of controlling insects which comprises applying, to the insects or their habitat, an insecticidally-effective amount of such a composition; such a method wherein the concentration of active ingredients in the composition is between about 1050 and 22,000 ppm by weight; such a method wherein the habitat is living plants; such a method wherein the plants are grasses, beans, corn, garden vegetables, fruits, or flowers; such a method wherein the plants are field corn, soybeans, sunflowers, or squash plants; such a method wherein the composition is applied by spraying; such a method wherein the composition is applied by aerial spraying; such a method wherein the weight ratio of (B) to (A) is between about 1:2.5 and 1:50 by weight; such a method wherein active ingredients are applied at a rate of about 0.17 to about 7.2 pounds per acre; such a method wherein the total composition is applied at a rate of about 24 to about 500 pounds per acre; such a method wherein the total composition is applied at a rate of about 80 to about 320 pounds per acre; such a method wherein the concentration of active ingredients is about 0.1 to 2.2 percent by weight of the total composition; such a method wherein the insect controlled is selected from Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips; such a method wherein (B) is oleoresin capsicum; such a method wherein the insect controlled is selected from the group consisting of Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips and the habitat protected is a plant selected from the group consisting of grasses, beans, corn, garden vegetables, fruits, and flowers.

Finally, a method of enhancing the insecticidal activity of (A) a synthetic surfactant composition comprising the step of including in said composition an effective insecticidal-activity-enhancing amount of (B) at least one capsaicinoid, the weight ratio of capsaicinoid to synthetic surfactant being between about 1:2.5 and 1:400 and the amount of capsaicinoid to total insecticidal composition, including both active and inactive ingredients, being between about 50 and 2000 parts per million by weight; such a method wherein the weight ratio is between about 1:25 and about 1:50 by weight and the amount of capsaicinoid to total insecticidal composition, including both active and inactive ingredients, is between about 100 and 400 parts per million by weight; such a method wherein the capsaicinoid comprises capsaicin; such a method wherein the capsaicin is in the form of an essentially lipid-free and optionally aqueous solution thereof in a polyol; such a method wherein (B) is at least one of capsaicin, norcapsaicin, dihydrocapsaicin, nordihydrocapsaicin, homodihydrocapsaicin, homocapsaicin, N-(4-hydroxy-3-methoxybenzyl) heptamide, N-(4-hydroxy-3-methoxybenzyl) octamide, N-(4-hydroxy-3-methoxybenzyl) nonamide, N-(4-hydroxy-3-methoxybenzyl) decamide, N-(4-hydroxy-3-methoxybenzyl) undecamide, and N-(4-hydroxy-3-methoxybenzyl) dodecamide; such a method wherein the capsaicinoid is in the form of an essentially lipid-free and optionally aqueous solution thereof in a polyol; such a method wherein the enhancement relates to the protection of a plant selected from the group consisting of grasses, beans, corn, garden vegetables, fruits, and flowers against an insect selected from the group consisting of Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips; and such a method wherein (B) is at least one capsaicinoid and (A) comprises a mixture of phosphate esters of alkylaryl poly (ethyleneoxy) ethanols of the formula

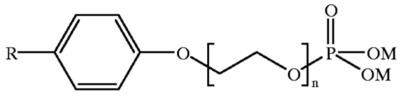

wherein $R=C_4H_9—C_{16}H_{33}$ alkyl, predominantly para oriented, n=4–15, $M=H$, Na, K, $NH_4$, $CH_3$, or $C_2H_5$, and phosphate esters of alkyl poly(ethyleneoxy) ethanols of the formula

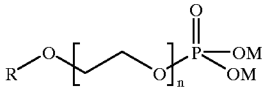

wherein $R=C_4H_9—C_{16}H_{33}$ alkyl, n=4–15, $M=H$, Na, K, $NH_4$, $CH_3$, or $C_2H_5$.

THE SYNTHETIC SURFACTANT INGREDIENT

Synthetic surfactants, as this term is employed herein, are certain man-made chemicals, described in further detail below, which possess surface active properties. They can be classified as anionic or nonionic in nature. In general, they consist of a relatively large hydrophobic group attached to a polar functionality, and examples covered in this application include alkyl, aryl and alkylaryl sulfonates; alkyl and alkylaryl phosphates; poly(oxyethylene) or poly(oxypropylene) derivatives of fatty alcohols, fatty acids, or alkylphenols; block copolymers of poly(oxyethylene) and poly (oxypropylene); esters of sulfosuccinic acid salts, and phosphate esters of alkylphenoxy poly(oxyethylene) ethanols employed individually or in admixture, as is sometimes the case.

In the book entitled "Insect Control by Chemicals" by A. W. A. Brown, John Wiley & Sons, Inc. (1951) in the chapter entitled "Insecticides of the Mid-Twentieth Century", under the heading "Soaps" at pages 46 and 47, the author describes the insecticidal properties of natural soap surfactants. In the following section, under the heading "Synthetic detergents", the author teaches that certain limitations of soaps can be overcome by replacing soaps with synthetic surfactants or detergents.

In a book entitled "Pesticide Applicator Core Training Manual" edited by J. Stachecki, Extension Bulletin E-2195, May 1995, Michigan State University Extension, on page 39, the author states that synthetic surfactants are commonly used as adjuvants, i.e., chemicals added to a pesticide formulation or tank mix to increase a pesticide's effectiveness or safety. The author further states that surfactants comprise some of the most common pesticide adjuvants and that, by their surface active properties, they alter the dispersing, spreading and wetting properties of spray droplets.

THE CAPSAICINOID INGREDIENT

The capsaicinoid ingredient according to the present invention is at least one and preferably a mixture of capsaicinoids derived from plants of the various Capsicum species, including capsaicin, identified in the Merck Index, 11th Edition, as number 1767, "Capsaicin", the trans-8-methyl-N-vanillyl-6-nonenamide; dihydrocapsaicin; norcapsaicin; nordihydrocapsaicin; homocapsaicin; and homodihydrocapsaicin. Other capsaicinoids, including synthetic capsaicinoids, such as the vanillyl amide of pelargonic acid, N-(4-hydroxy-3-methoxybenzyl) heptamide, N-(4-hydroxy-3-methoxybenzyl) octamide, N-(4-hydroxy-3-methoxybenzyl) decamide, N-(4-hydroxy-3-methoxybenzyl) undecamide, and N-(4-hydroxy-3-methoxybenzyl) dodecamide may also be employed, inasmuch as these have the same irritating and noxious properties as natural capsaicinoids and especially capsaicin. The stereoisomer of capsaicin, the cis compound, may also be employed but is not preferred inasmuch as it is less irritating than the trans isomer.

The following is the preferred form of capsaicin and capsaicinoids, which makes them more conveniently dispersible/soluble in water.

Capsyn®—A solution of capsaicinoids in propylene glycol, prepared by partitioning oleoresin capsicum with propylene glycol, essentially free of lipids and fats, carotenoids, and capsicum triglycerides (i.e., defatted oleoresin capsicum in propylene glycol), and containing about 2% capsaicinoids obtained from capsicum pepper pods, a product of Kalsec, Inc., Kalamazoo, Mich. (EPA Reg. No. 43889-1.)

An essentially lipid-free and optionally aqueous solution of capsaicin and/or other capsaicinoid in a polyol such as ethylene glycol, propylene glycol, glycerine, or the like, but preferably in propylene glycol, is therefore the preferred form for ready dispersibility and employment according to the method and composition of the invention.

THE PRESENT INVENTION

According to the present invention, the synergistic effect of the insecticidal combination of the present invention is demonstrated by the following Examples, which also show that neither the synthetic surfactant nor the capsaicinoids are outstanding insecticides by themselves, but that direct admixture and application together produces synergistically enhanced kill rates and effective kill rates which extend over periods of time which are many times greater than the periods of effective kill rates for the individual components.

According to the present invention, the admixtures or combinations of the present invention may be applied to the insect or its habitat as by spraying, dusting, or the like.

The preferred form of capsaicinoids is Capsyn®, which is a solution of the capsaicinoids from oleoresin capsicum derived from Capsicum sp. partitioned into propylene glycol, being essentially free of triglycerides, fats, and carotenoids. It is water dispersible and the combination of the Capsyn® and the synthetic surfactant according to the present invention remains in aqueous solution or suspension as a cloudy admixture. It does not leave a residual color on plant material, such as cotton. In less preferred forms, this may be the case. For instance, in a less preferred form of an oil solution of the oleoresin capsicum extract, optionally but preferably emulsified with an emulsifier such as Polysorbate 80®, the oil solution may sometimes somewhat interfere with the effect of emulsifier when and if employed for dispersion or emulsification of the insecticidal composition and, moreover, may sometimes stain the foliage as well as develop rancid aromas which, of course, is the exact reason why such oil solutions are not preferred.

The combinations or admixtures of the invention are active against a wide range of insects, and one of their advantages stems from the fact that they can be applied to a crop attacked by insects at any stage of their life cycle, although clearly the compositions of the present invention are more effective against insects during stages 2 and 3 of their life cycle, that is, the rapidly growing and feeding juvenile stage or the adult stage of their development. The flexibility of the compositions of the present invention in this respect is an important advantage since timing of insecticide application thus becomes less critical and there is a greater chance of obtaining good overall control with only a single treatment, especially since not only is the activity of the individual components enhanced synergistically in the combination but since a far-reaching and totally unexpected extension of the period of effectiveness, that is, the period of effective kill rates after a single application, is observed.

The composition and method of the present invention thus exhibit not only an enhanced insecticidal effectiveness far beyond that attained with the individual components themselves but also the totally unpredicted extension of period of effectiveness, that is, from an effective kill level at only one day after application to an effective kill level fourteen days after a single application, certainly a most important factor in insect control.

Included in the list of insects against which the enhanced and extended insecticidal activity is provided according to the present invention are the following: Fall Army Worms, Alfalfa Weevils, Corn Ear Worms, Corn Leaf Aphids, True Army Worms, Grasshoppers, Potato Leaf Hoppers, Beanleaf Beetles, and Soybean Thrips. In addition, inter alia, although possibly to a somewhat lesser extent, the Corn Flea Beetle, Stink Bugs, and the European Corn Borer may be controlled, especially at their stage 2 and stage 3 developmental levels, as well as True Army Worm at its second stage of development, Grasshopper in its third stage of development, Potato Leaf Hopper in its second stage of development, and Beanleaf Beetle in its third stage of development. Although the insecticidal control of the foregoing insects has been established in actual field tests on various plants such as weeds, grasses, beans, corn, garden vegetables, fruits, and flowers, especially field corn, soybeans, sunflowers, and squash, the foregoing types of insects susceptible to treatment with the compositions of the present invention and according to the method of the invention are merely representative as are the crops or plants comprising the habitat or environment in which the insects are found to be located.

When employing a composition of the invention, the essential ingredients, namely, the capsaicinoid and the synthetic surfactant, are conveniently admixed together in a ratio ranging from about 1:2.5 to 1:400, preferably ranging from 1:10 to 1:200, and especially ranging from 1:25 to 1:50 by weight. The amount of capsaicinoid to total insecticide composition by weight (including both active and inactive ingredients) is generally between about 50 and 2000 parts per million and preferably between about 100 and 400 parts per million. Application of the compositions of the invention in an aqueous or water solution or suspension may conveniently be carried out by preparing a spray mix containing 0.01 or 0.02 gallons of capsicum extract in the form of Capsyn® per gallon of water and 1, 2 or 3 ounces of the selected synthetic surfactant, e.g., in the form of Inhance®, per gallon of water and applying the spray mix at a rate of about 20 gallons per acre.

The composition of the invention can be employed in a wide variety of forms and can comprise a liquid or solid diluent. It is most conveniently prepared in aqueous form immediately prior to use, for example, as a spray for insect-infested crops. One such method is commonly called "tank mixing" in which the two essential ingredients in their commercially-available forms are mixed together by the farmer or entomologist in the quantity of water most useful for the direct application. The concentration of the essential ingredients for application to a crop by conventional ground methods is preferably within the range of about 0.1 to 2.2 percent, especially about 0.5 to 1.1 percent by weight of the total composition (including both active and inactive ingredients), but more concentrated compositions containing up to 5 percent by weight may be desirable in the case of aerial sprays but with corresponding loss in economy. Concerning amounts of water: The amount of water used in conjunction with the synthetic surfactant. and Capsyn™ can be adjusted upwardly or downwardly, as the particular application and available equipment require. In terms of pounds per acre of active ingredients, effective rates are between about 0.17 and 7.2 pounds per acre and the total composition is advantageously applied at a rate of about 24 to 500 pounds per acre.

The compositions of the invention include not only those in suitable form for direct application but also concentrated primary compositions which can be supplied to the user for on-site dilution with a suitable quantity of water or other diluent before application. Typical examples are an aqueous solution, an aqueous dispersion or suspension, an aqueous emulsion, a concentrate emulsifiable in water, a dispersible powder, or a dusting powder. In such a concentrated primary composition or "concentrate", the concentration of essential ingredients to be "let down" by addition of water or other diluting fluid, including for some applications a finely-divided powder, can vary widely and can be for example from 5 to 95 percent by weight of the composition, as is well known in the art.

An emulsifiable concentrate, also known as a "miscible liquid", comprises a solution of the essential ingredients at least partially in a water-immiscible solvent, optionally in association with one or more emulsifying agents. An emulsion is then formed when the emulsifiable concentrate is let down by dilution with water.

A dispersible powder comprises the essential ingredients in finely-divided pulverulent form, optionally in association with one or more dispersing agents, so that a stable aqueous dispersion of the essential ingredients is formed upon mixing the powder with water. A finely-divided inert solid diluent such as kaolin or CELITE (diatomalesus earth) is generally incorporated in the dispersible powder. A dusting powder comprises the essential ingredients intimately admixed with a solid pulverulent diluent, for example kaolin. Concerning dusts, etc.: Capsaicinoids and synthetic surfactants can be incorporated into dusts and other non-aqueous systems by using the dry active capsaicinoids in anhydrous form, or in a suitable oil base.

As a further aspect, the invention includes a method of controlling insects which comprises applying a composition comprising the synthetic surfactant and the activity-enhancing and extending capsaicinbid (or vice versa) to the locus of the insects, that is, to the insects or their habitat, including the surrounding area. More particularly, the invention comprises a method for protecting plants, especially growing plants or crops, from insects by the use of such compositions applied most conveniently as a foliar spray.

BRIEF DESCRIPTION OF THE DRAWINGS

Reference is now made to the drawings for a better understanding of the invention, wherein the figures portray the effect of the capsaicinoid and synthetic surfactant combination on a variety of insects with the kill level being plotted against the time in hours for capsaicinoid alone, the surfactant alone, the actual capsaicinoid plus surfactant result, and the calculated capsaicinoid plus surfactant result, and in which FIG. 1 portrays the effect upon Fall Army Worms—stage 3, average of all doses as shown in Example 1, FIG. 2 portrays the effect upon Fall Army Worms—stage 2, average of all doses as shown in Example 1, FIG. 3 portrays the effect upon Alfalfa Weevils—stage 3, average of all doses as shown in Example 2, FIG. 4 portrays the effect upon Alfalfa Weevils—stage 2, average of all doses as shown in Example 2, FIG. 5 portrays the effect upon Corn Ear Worms—stage 3, average of all doses as shown in Example 3, FIG. 6 portrays the effect upon Corn Ear Worms—stage 2, average of all doses as shown in Example 3, FIG. 7 portrays the effect upon Corn Leaf Aphid—stage 3, average of all doses as shown in Example 4, FIG. 8 portrays the effect upon Corn Leaf Aphid—stage 2, average of all doses as shown in Example 4, FIG. 9 portrays the effect upon Potato Leaf Hopper—stage 3, average of all doses as shown in Example 5, FIG. 10 portrays the effect upon Bean Leaf Beetle—stage 2, average of all doses as shown in Example 6, FIG. 11 portrays the effect upon Soybean Thrips—stage 3, as shown in Example 7, FIG. 12 portrays the effect upon Soybean Thrips—stage 2, as shown in Example 8, FIG. 13 portrays the effect upon True Army Worms—stage 3, average of all doses as shown in Example 9, and FIG. 14 portrays the effect upon Grasshopper—stage 2, average of all doses as shown in Example 10.

Further details are to be found in the respective Examples themselves.

DETAILED DESCRIPTION OF THE INVENTION

Figure 1:
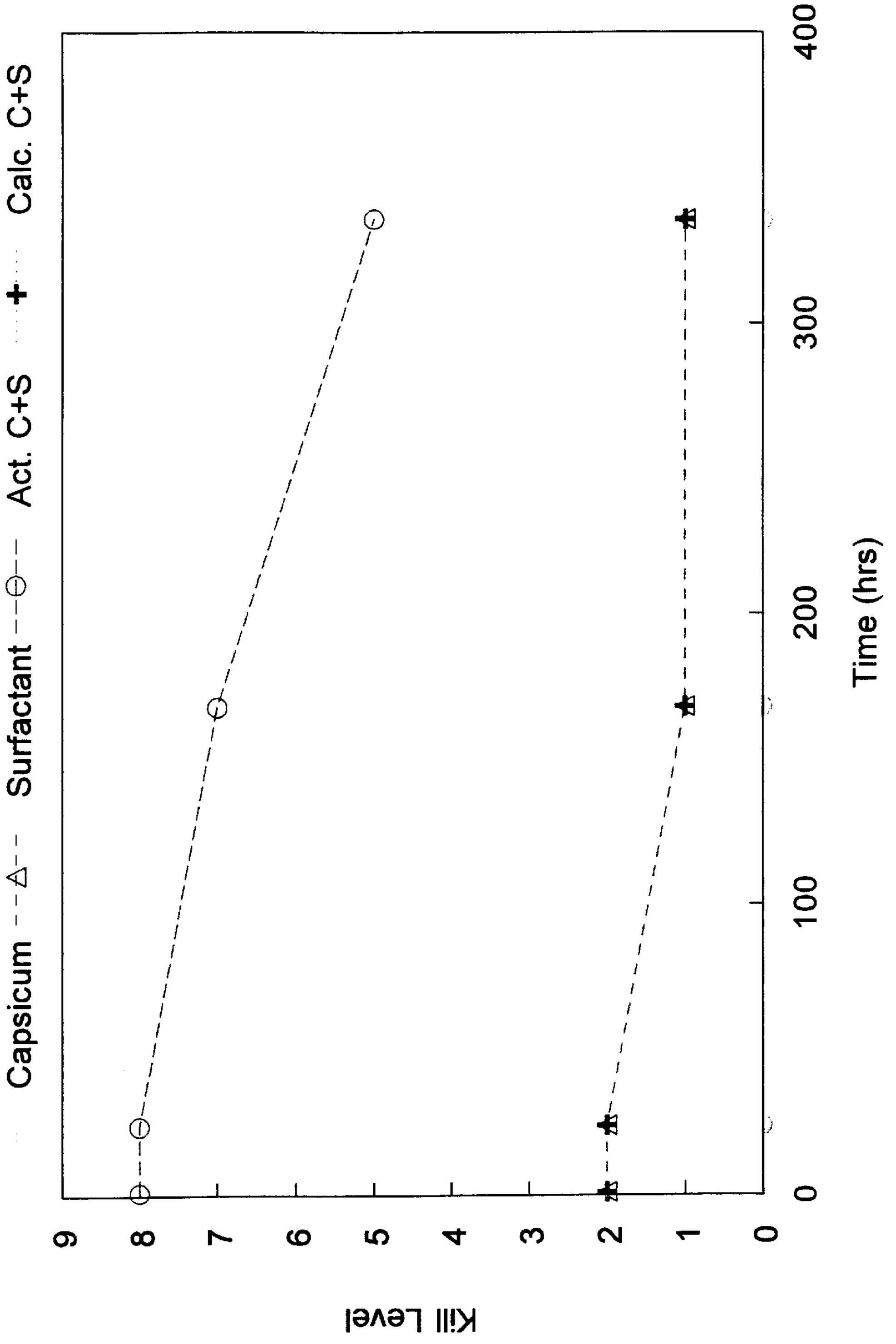

The following Examples are given by way of illustration only, and are not to be construed as limiting.

General Method for Examples 1–10.

A weed host environment in the form of plots containing a mixture of Weeds, Sunflowers, Squash, Soybeans, and Field Corn, in a randomized complete block was used for the study. Plots were three meters wide, ten meters long, separated by seven feet, and isolated from each other using hay bales. They provided excellent vegetation for insect entrapment. Various insecticidal formulations were applied using a commercial hand-held sprayer, with each treatment being replicated three times on random plots within the block. A control section received no insecticidal treatment. Kill levels were determined one hour, twenty-four hours, seven days and fourteen days after application by a trained entomologist using a visual inspection method. An insect census was performed with dead insects being removed and identified using a suction trap. Kill levels are based on a scale of 0–10, with 0=no kill and 10=total kill. The effect of the treatments on both stage 2 (rapidly growing and feeding) and stage 3 (adult) developmental levels of the insects were noted. The insecticidal treatments were:

1) No treatment—control

2) Mixtures of a commercial capsicum extract in the form of Capsyn® and water. Three different application rates containing 132, 200, and 400 ppm capsaicinoids were tested at application rates of 20 gallons of spray mix per acre.

3) A mixture of a commercial synthetic surfactant in the form of Inhance®, the essential ingredient of which comprises a mixture of phosphate esters of alkylaryl poly(ethleneoxy) ethanols of the formula

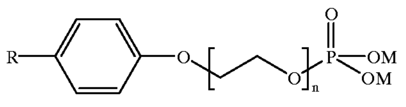

wherein R=$C_4H_9$—$C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

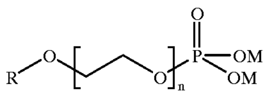

wherein R=$C_4H_9$—$C_{16}H_{33}$ alkyl, n=4–15,

M=H, Na, K, $NH_4$, $CH_3$, or $C_2H_5$, and which also comprises ammonium and sulfate ions, and water, providing 3125 ppm active ingredient at the rate of 20 gallons of spray mix per acre.

4) Mixtures of capsicum extract in the form of Capsyn® plus synthetic surfactant in the form of Inhance® and water. The amount of synthetic surfactant active ingredient in these tests was maintained at 3125 ppm. Three different application rates, namely 132, 200, and 400 ppm capsaicinoids were tested. Application rates were 20 gallons per acre.

Data Treatment

The kill levels for the treatments containing capsaicinoids from commercial capsicum extract Capsyn® were averaged over both replicates and application rates, providing a single average kill level at each inspection time. The data was separated according to the developmental level of the insect in question. Often, as with other insecticides, the effects of the treatments differed considerably, depending among other things on whether the insect was in stage 2 or stage 3 of development. Kill levels for. each treatment were plotted as a function of time and the effect of each treatment was compared.

Example 1. Effect on Fall Army Worms

On stage 3 (adult) fall army worms, both capsaicinoid and synthetic surfactant Inhance® treatments alone proved to be relatively ineffective. Capsaicinoid treatments provided zero kill level at all inspection times. The synthetic surfactant treatment was only slightly more effective, giving initial kill levels of 2 and final kill levels of 1, as shown in FIG. 1. However, when capsaicinoids from the capsicum extract and the synthetic surfactant were combined, the result was highly synergistic. Kill levels of 8 were observed one hour and twenty-four hours after application. The effectiveness was only slightly diminished seven days and fourteen days after application.

| | Kill Levels Stage 3 | | | |
|---|---|---|---|---|
| Fall Army Worm Time | Capsaicinoids | Surfactant | Theoretical Capsaicinoids + Surfactant | Actual Capsaicinoids + Surfactant |
| 1 hour | 0 | 2 | 2 | 8 |
| 24 hours | 0 | 2 | 2 | 8 |
| seven days | 0 | 1 | 1 | 7 |
| fourteen days | 0 | 1 | 1 | 6 |

Figure 2:
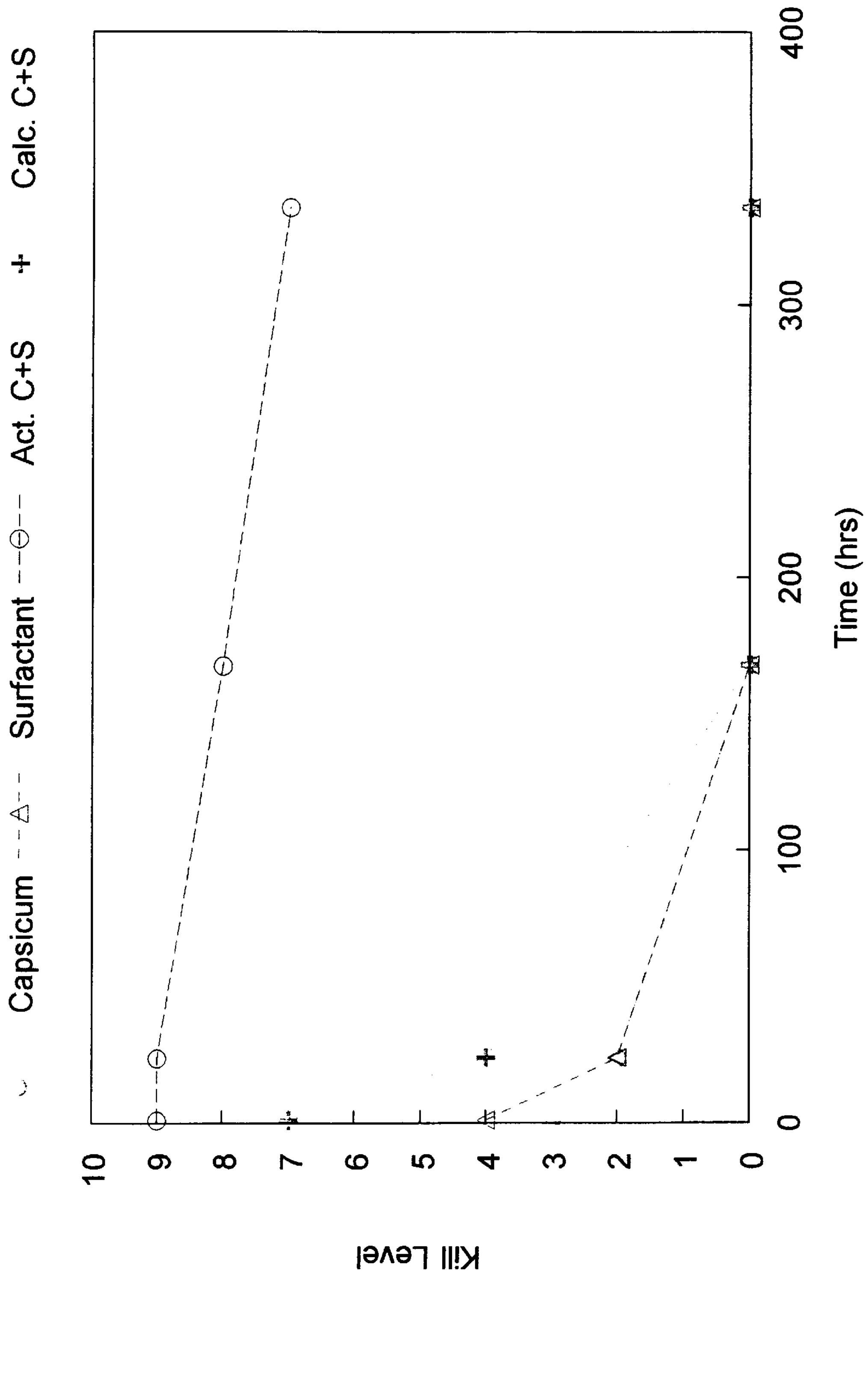

On stage 2 (juvenile) fall army worms, separate capsaicinoid and synthetic surfactant (Inhance®) treatments showed similar activity. Kill levels were about three to four, initially, but dropped to zero at seven and fourteen days after application. The capsaicinoid plus synthetic surfactant combination showed very high initial activity (kill level=9) which dropped only slightly at seven and fourteen days (FIG. 2). Although not showing initial synergistic activity as dramatic as on the stage 3 fall army worms, this example illustrates the striking and surprising extension of activity which the combination of capsaicinoids and synthetic surfactant affords.

| | Kill Levels Stage 2 | | | |
|---|---|---|---|---|
| Fall Army Worm Time | Capsaicinoid | Surfactant | Theoretical Capsaicinoid + Surfactant | Actual Capsaicinoid + Surfactant |
| 1 hour | 3 | 4 | 7 | 9 |
| 24 hours | 2 | 2 | 4 | 9 |
| seven days | 0 | 0 | 0 | 8 |
| fourteen days | 0 | 0 | 0 | 7 |

Essentially the same result is obtained when using synthetic capsaicinoids in place of natural capsaicinoids, especially N-(4-hydroxy-3-methoxybenzyl) nonamide or the corresponding heptamide or octamide.

Example 2. Effect on Alfalfa Weevils

Figure 3:
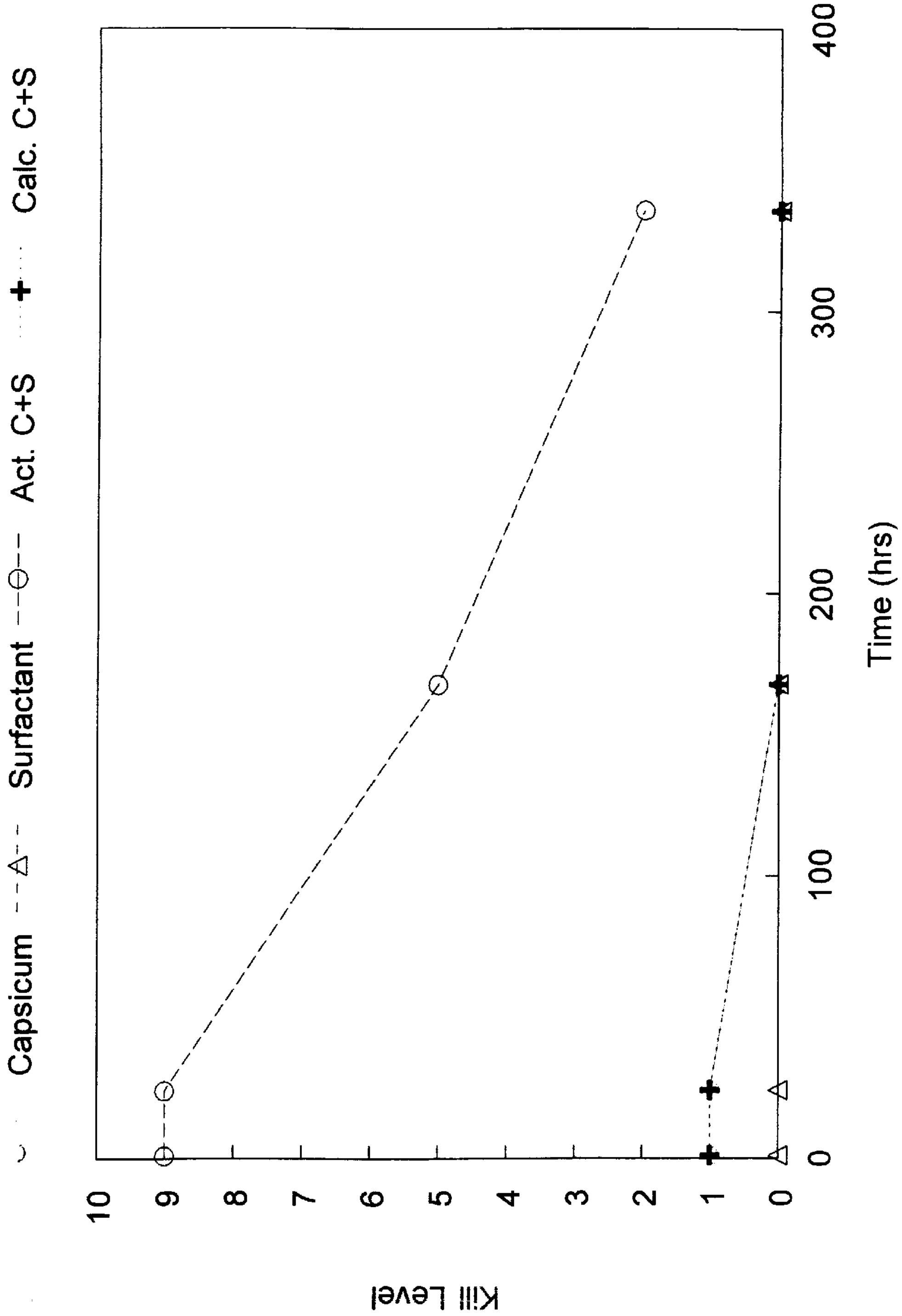

The combination of capsaicinoids from the capsicum extract and synthetic surfactant (Inhance®) provides a highly synergistic combination on stage 3 alfalfa weevils. The initial kill level of 9 is much higher than the levels of either component individually (synthetic surfactant kill level=0, capsicum extract kill level=1). Once again, the dramatic extension of activity through day 14 is observed (FIG. 3).

| | Kill Levels Stage 3 | | | |
|---|---|---|---|---|
| Alfalfa Weevils Time | Capsaicinoids | Surfactant | Theoretical Capsaicinoids + Surfactant | Actual Capsaicinoids + Surfactant |
| 1 hour | 1 | 0 | 1 | 9 |
| 24 hours | 1 | 0 | 1 | 9 |
| seven days | 0 | 0 | 0 | 5 |
| fourteen days | 0 | 0 | 0 | 2 |

Figure 4:
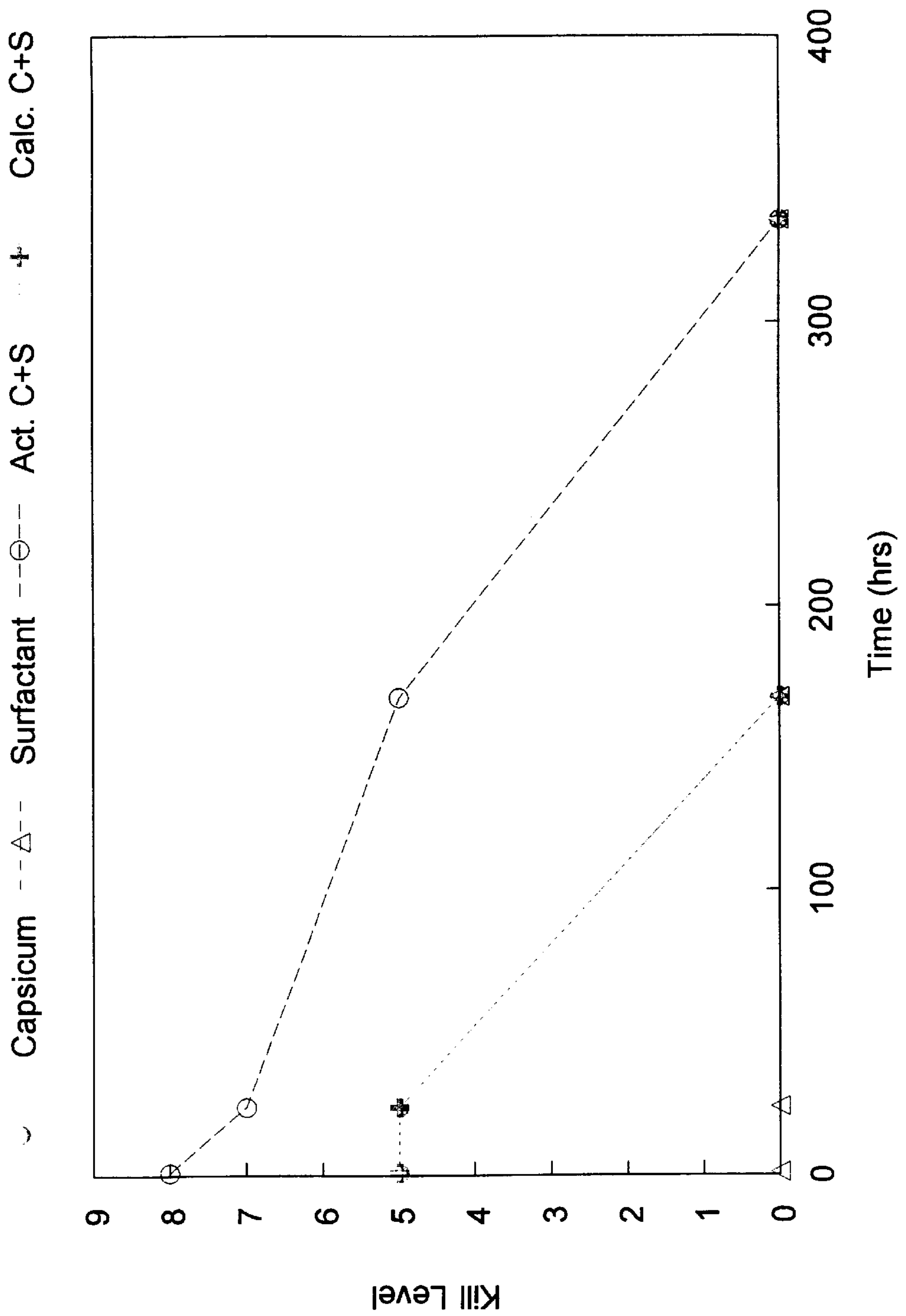

On stage 2 alfalfa weevils, the initial synergism is not as pronounced. The extension of activity is observed again. (FIG. 4.).

| | Kill Levels Stage 2 | | | |
|---|---|---|---|---|
| Alfalfa Weevils Time | Capsaicinoids | Surfactant | Theoretical Capsaicinoids + Surfactant | Actual Capsaicinoids + Surfactant |
| 1 hour | 5 | 0 | 5 | 8 |
| 24 hours | 5 | 0 | 5 | 7 |
| seven days | 0 | 0 | 0 | 5 |
| fourteen days | 0 | 0 | 0 | 0 |

Example 3 . Effect on Corn Earworms

Figure 5:
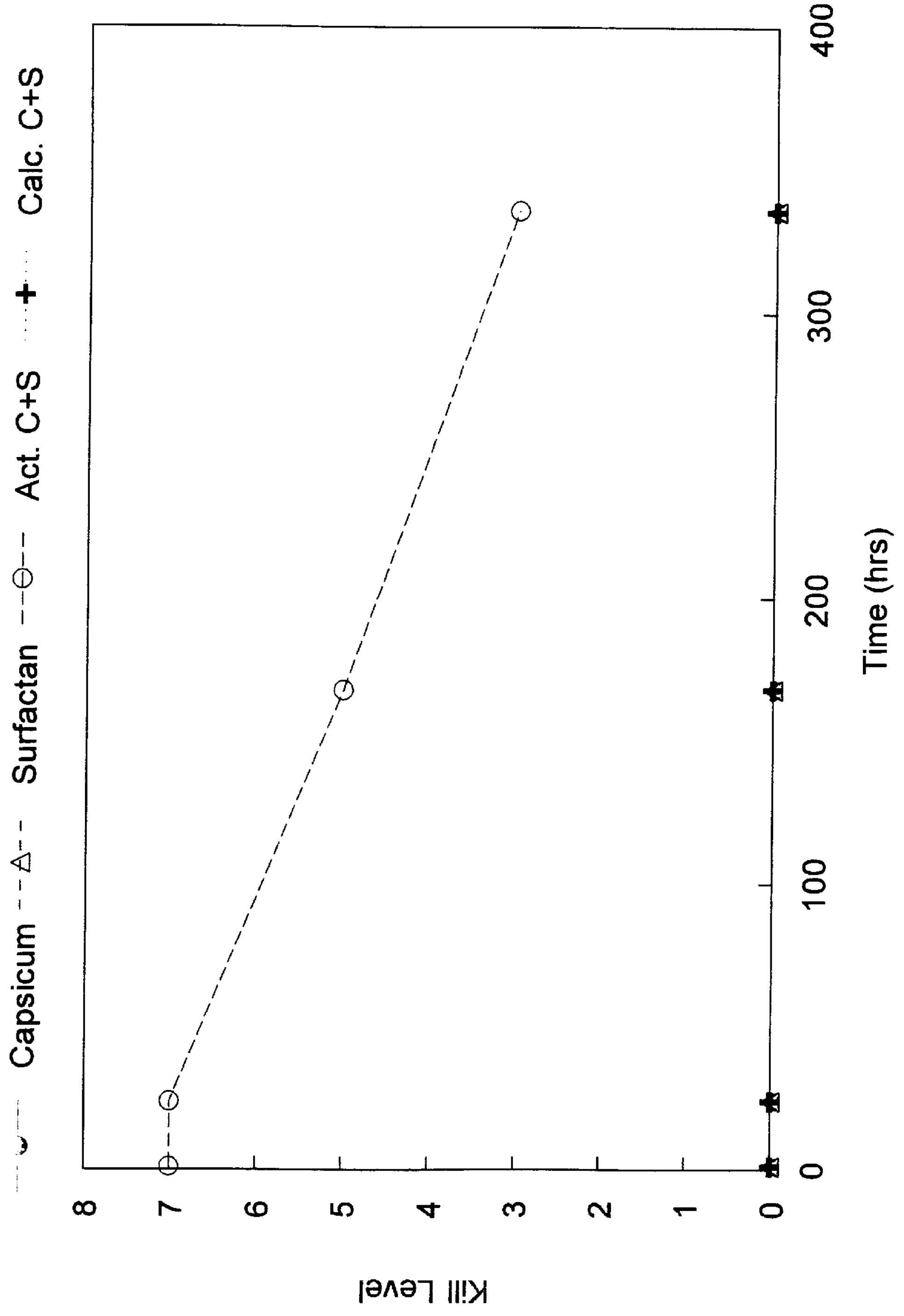

The combination of capsaicinoids from the capsicum extract and synthetic surfactant (Inhance®) provides a highly synergistic combination on stage 3 alfalfa weevils. Separate treatments show no activity at all but, in combination, the kill level is high. Once again, the dramatic extension of activity through day 14 is observed (FIG. 5).

| | Kill Levels Stage 3 | | | |
|---|---|---|---|---|
| Corn Earworms Time | Capsaicinoid | Surfactant | Theoretical Capsaicinoid + Surfactant | Actual Capsaicinoid + Surfactant |
| 1 hour | 0 | 0 | 0 | 7 |
| 24 hours | 0 | 0 | 0 | 7 |
| seven days | 0 | 0 | 0 | 5 |
| fourteen days | 0 | 0 | 0 | 3 |

Figure 6:
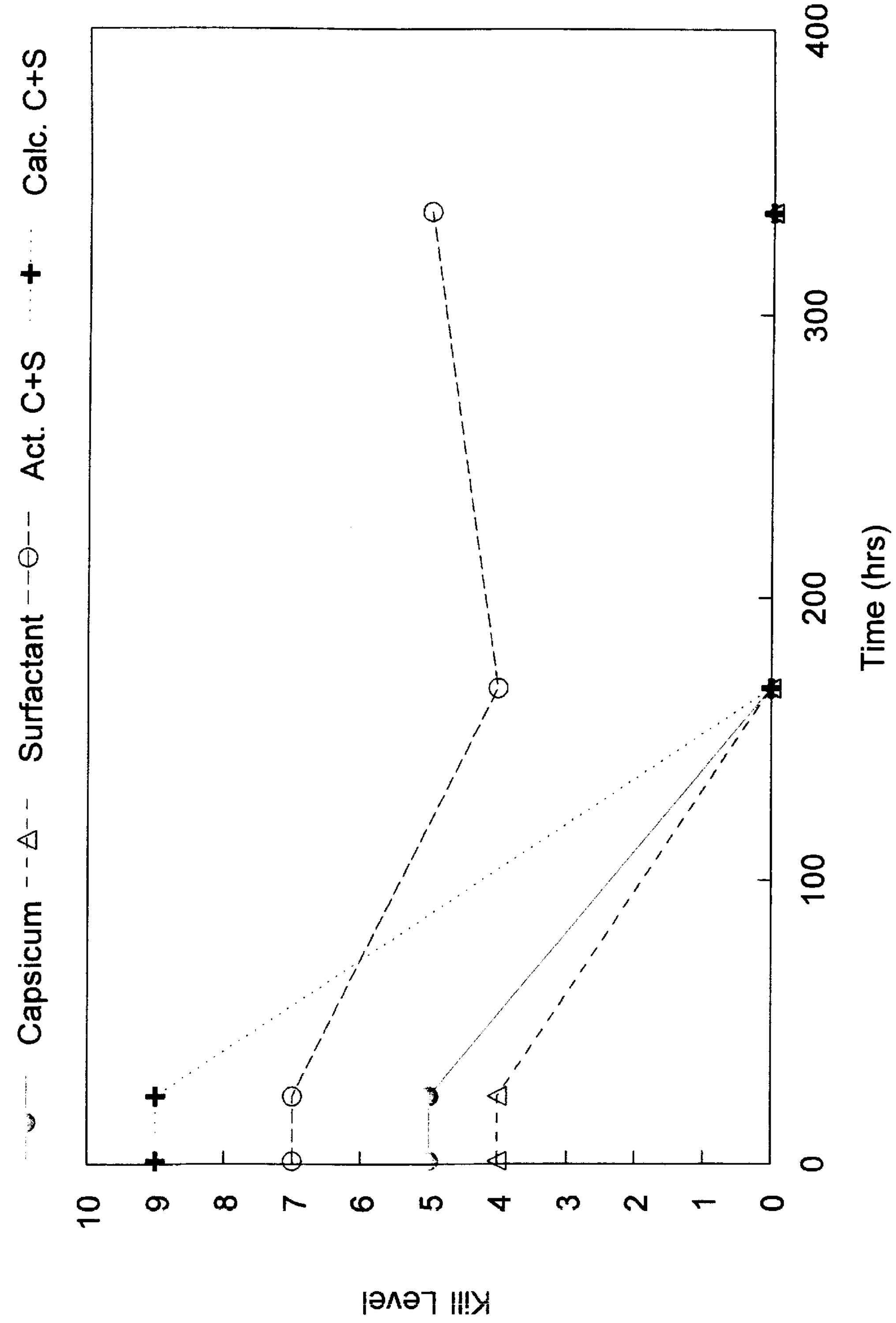

On stage 2 corn earworms, the kill level of the combination is extended out to fourteen days in spite of the fact that the combination is not truly synergistic an hour or a day after application (FIG. 6). The rise in kill level from day seven to day fourteen is probably an indication of the experimental variability of the data, but the general trend shows an extension of the length of the effect. The variability in no way invalidates the trend of the data.

| | Kill Levels Stage 2 | | | |
|---|---|---|---|---|
| Corn Earworms Time | Capsaicinoid | Surfactant | Theoretical Capsaicinoid + Surfactant | Actual Capsaicinoid + Surfactant |
| 1 hour | 5 | 4 | 9 | 7 |
| 24 hours | 5 | 4 | 9 | 7 |
| seven days | 0 | 0 | 0 | 4 |
| fourteen days | 0 | 0 | 0 | 5 |

Example 4. Effect on Corn Leaf Aphids

Figure 7:
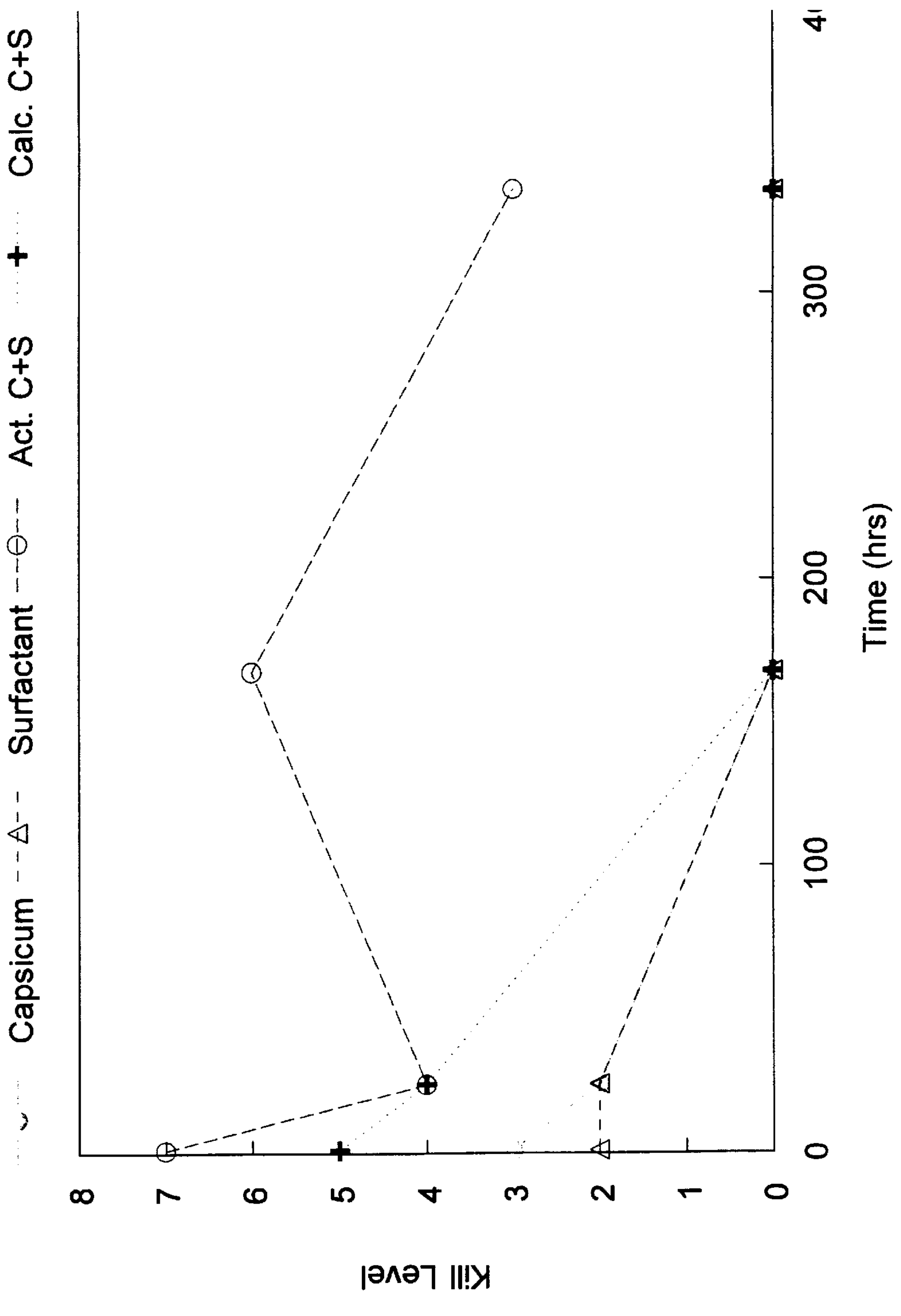

A combination of capsaicinoids from the capsicum extract and synthetic surfactant (Inhance®) shows enhanced activity over the sum of the activity of the individual components. The activity is extended out to fourteen days. The increase in kill level between day one and day seven probably reflects the variability in the experimental data (FIG. 7).

| | Kill Levels Stage 3 | | | |
|---|---|---|---|---|
| Corn Leaf Aphids Time | Capsaicinoid | Surfactant | Theoretical Capsaicinoid + Surfactant | Actual Capsaicinoid + Surfactant |
| 1 hour | 3 | 2 | 5 | 7 |
| 24 hours | 2 | 2 | 4 | 4 |
| seven days | 0 | 0 | 0 | 6 |
| fourteen days | 0 | 0 | 0 | 3 |

Figure 8:
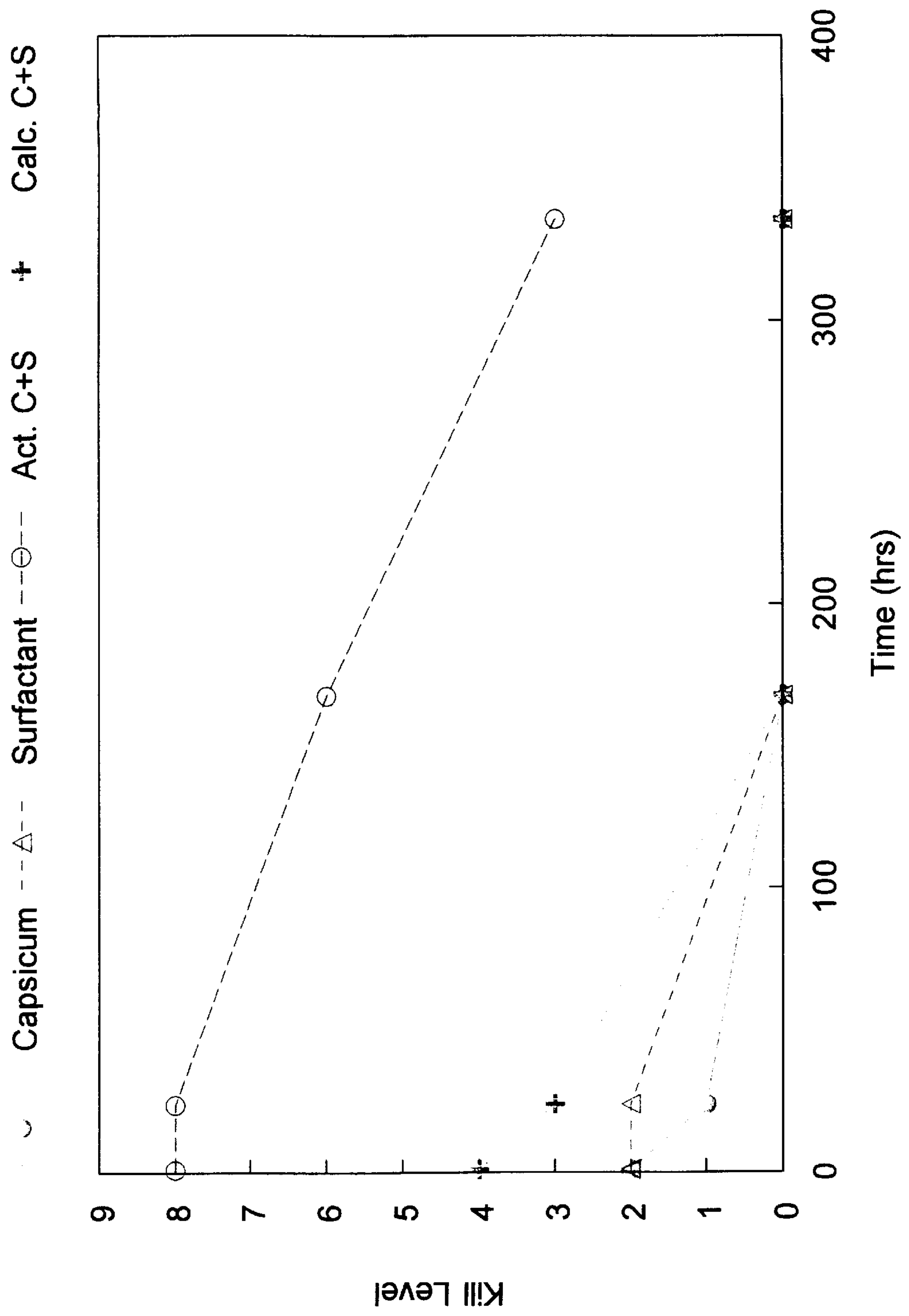

A truly synergistic effect is shown on stage 2 corn leaf aphids. The combination shows at least double the activity one would expect by summing the activities of the individual components. Once again, the highly favorable extension of activity out to day fourteen is observed (FIG. 8).

| | Kill Levels Stage 2 | | | |
|---|---|---|---|---|
| Corn Leaf Aphids Time | Capsaicinoid | Surfactant | Theoretical Capsaicinoid + Surfactant | Actual Capsaicinoid + Surfactant |
| 1 hour | 2 | 2 | 4 | 8 |
| 24 hours | 1 | 2 | 3 | 8 |
| seven days | 0 | 0 | 0 | 6 |
| fourteen days | 0 | 0 | 0 | 3 |

Example 5. Effect on Potato Leaf Hopper—Stage 3

Figure 9:
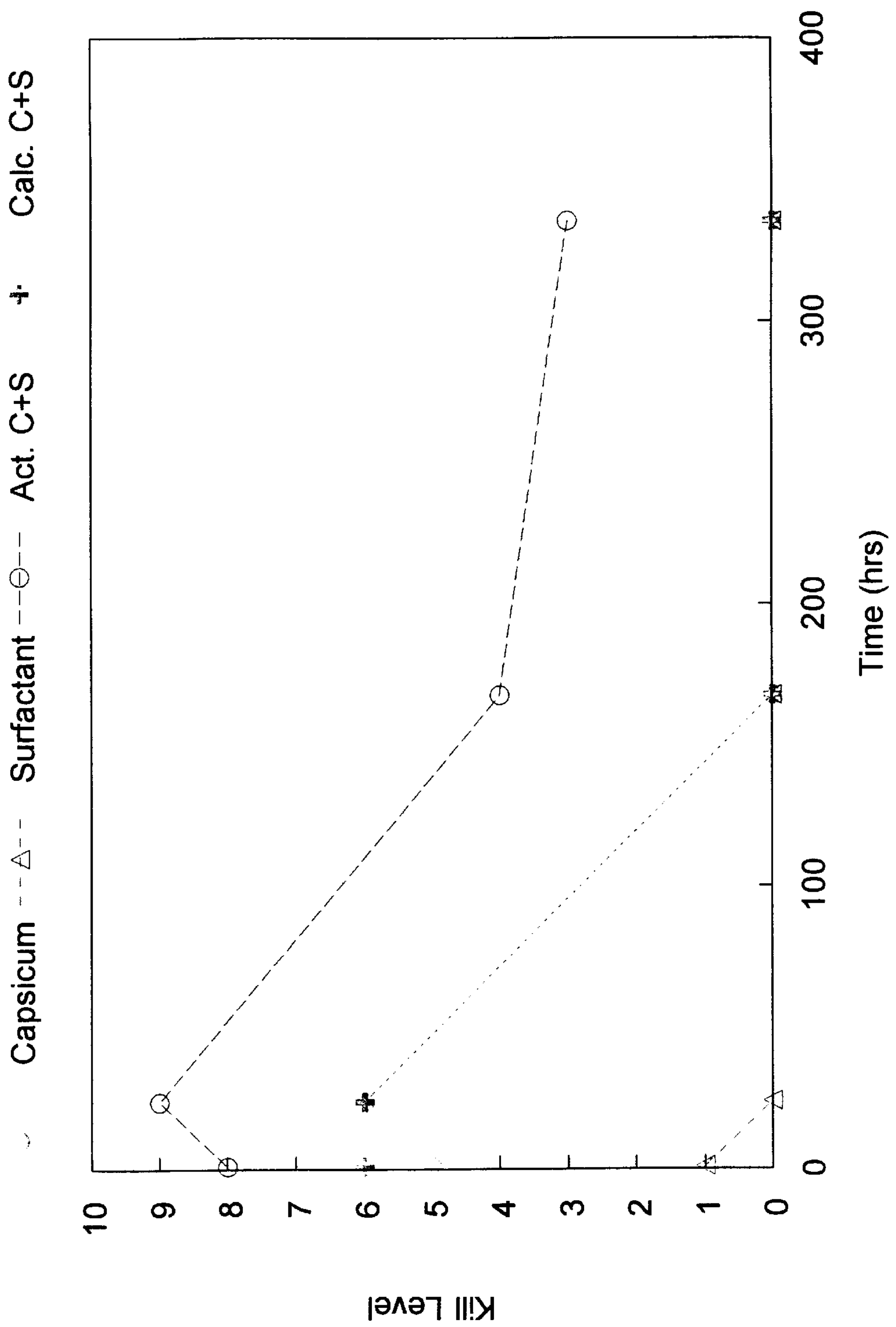

On stage 3 potato leaf hopper, the kill level of the combination is greater than calculated after one hour and after twenty-four hours and is extended out to fourteen days after application as depicted in FIG. 9.

| Potato Leaf Hopper Time | Kill Levels Stage 3 | | | |
|---|---|---|---|---|
| | Cap-saicinoid | Surfactant | Theoretical Cap-saicinoid + Surfactant | Actual Cap-saicinoid + Surfactant |
| 1 hour | 5 | 1 | 6 | 8 |
| 24 hours | 6 | 0 | 6 | 9 |
| seven days | 0 | 0 | 0 | 4 |
| fourteen days | 0 | 0 | 0 | 3 |

Example 6. Effect on Stage 2 Bean Leaf Beetle

Figure 10:
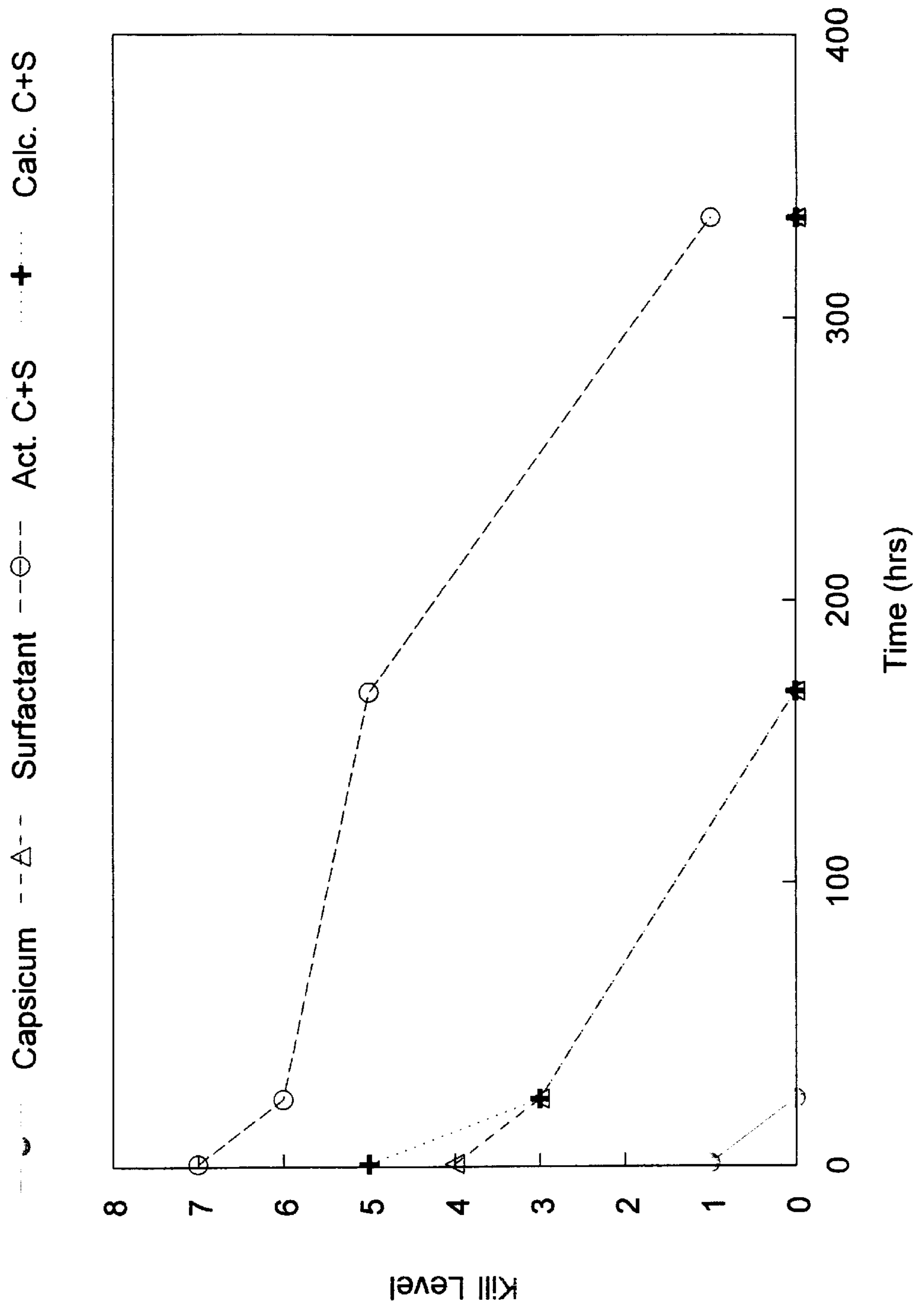

On stage 2 bean leaf beetle, the kill level of the combination is greater than calculated after one hour and after twenty-four hours and is extended out to fourteen days after application as shown in FIG. 10.

| Bean Leaf Beetle Time | Kill Levels Stage 2 | | | |
|---|---|---|---|---|
| | Cap-saicinoid | Surfactant | Theoretical Cap-saicinoid + Surfactant | Actual Cap-saicinoid + Surfactant |
| 1 hour | 1 | 4 | 5 | 7 |
| 24 hours | 0 | 3 | 3 | 6 |
| seven days | 0 | 0 | 0 | 5 |
| fourteen days | 0 | 0 | 0 | 1 |

Example 7. Effect on Stage 3 Soybean Thrips

Figure 11:
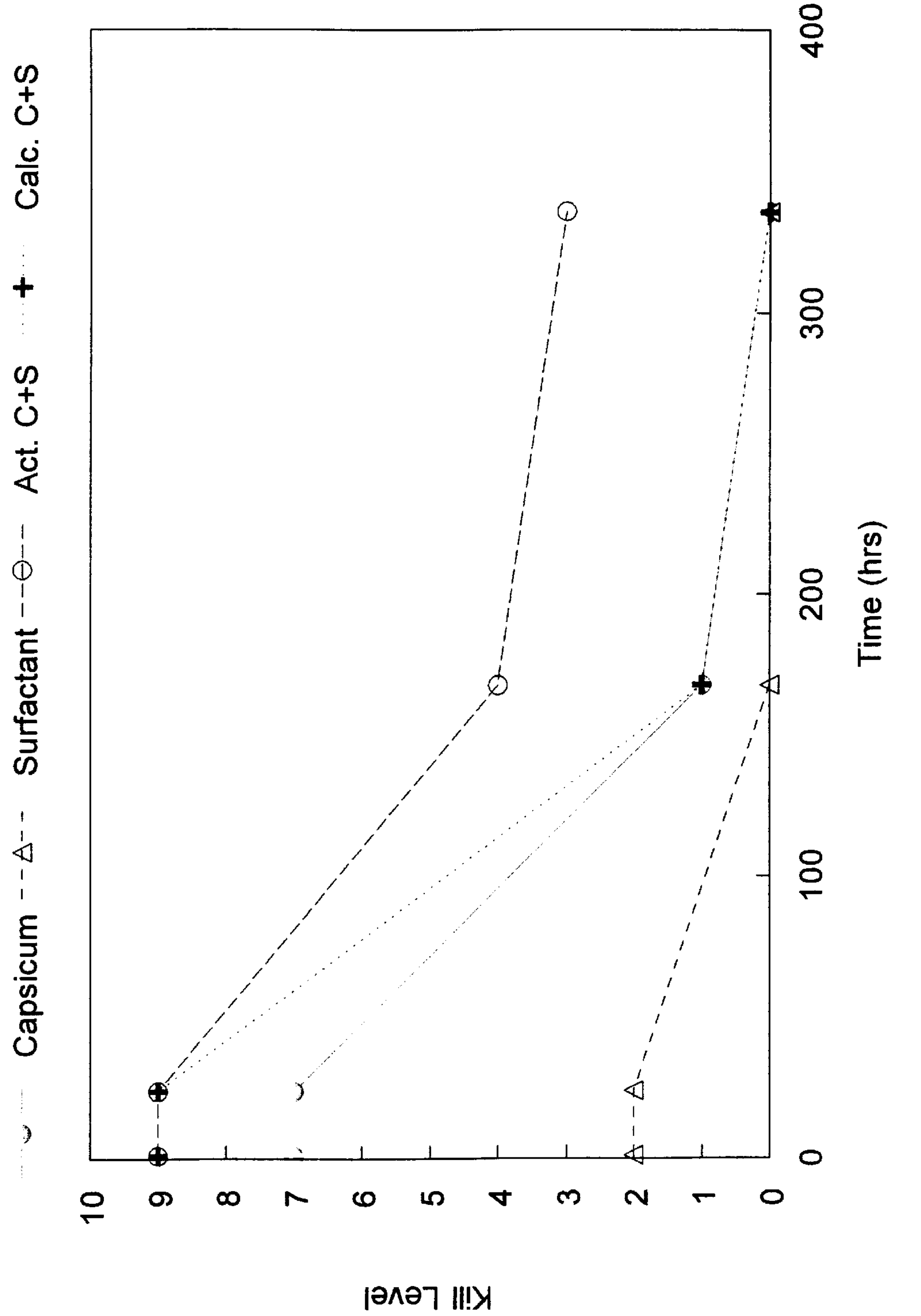

On stage 3 soybean thrips, the kill level of the combination is not greater than calculated after one hour and after twenty-four hours, but is unexpectedly extended out to fourteen days after application as shown in FIG. 11.

| Soybean Thrips Time | Kill Levels Stage 3 | | | |
|---|---|---|---|---|
| | Cap-saicinoid | Surfactant | Theoretical Cap-saicinoid + Surfactant | Actual Cap-saicinoid + Surfactant |
| 1 hour | 7 | 2 | 9 | 9 |
| 24 hours | 7 | 2 | 9 | 9 |
| seven days | 1 | 0 | 1 | 4 |
| fourteen days | 0 | 0 | 0 | 3 |

Example 8. Effect on Stage 2 Soybean Thrips

Figure 12:
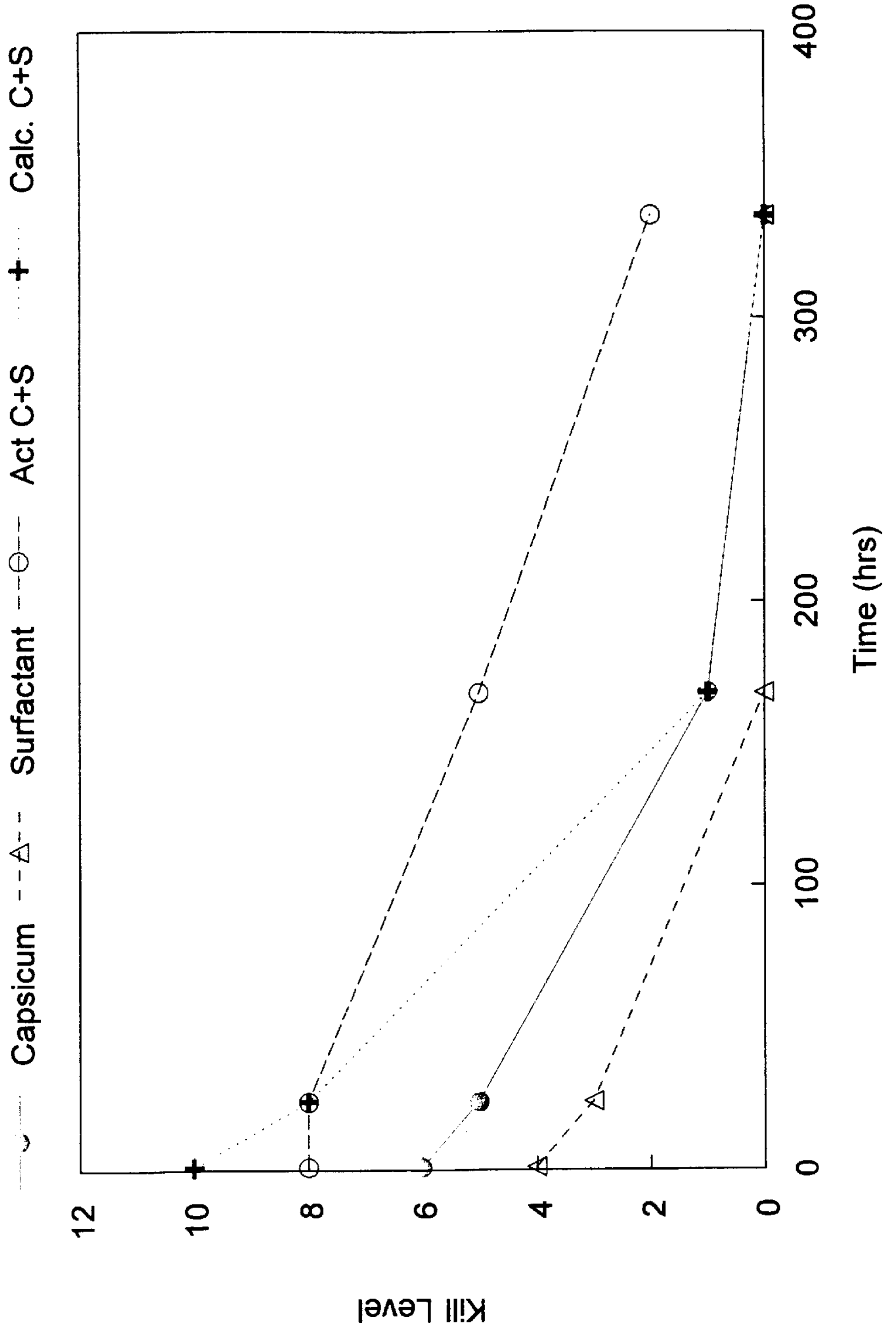

On stage 2 soybean thrips, the kill level does not exceed the calculated after one hour and after twenty-four hours, but is unpredictably extended out to fourteen days after application as depicted in FIG. 12.

| Soybean Thrips Time | Kill Levels Stage 2 | | | |
|---|---|---|---|---|
| | Cap-saicinoid | Surfactant | Theoretical Cap-saicinoid + Surfactant | Actual Cap-saicinoid + Surfactant |
| 1 hour | 6 | 4 | 10 | 8 |
| 24 hours | 5 | 3 | 8 | 8 |
| seven days | 1 | 0 | 1 | 5 |
| fourteen days | 0 | 0 | 0 | 2 |

Example 9. Effect on Stage 3 True Army Worms

Figure 13:
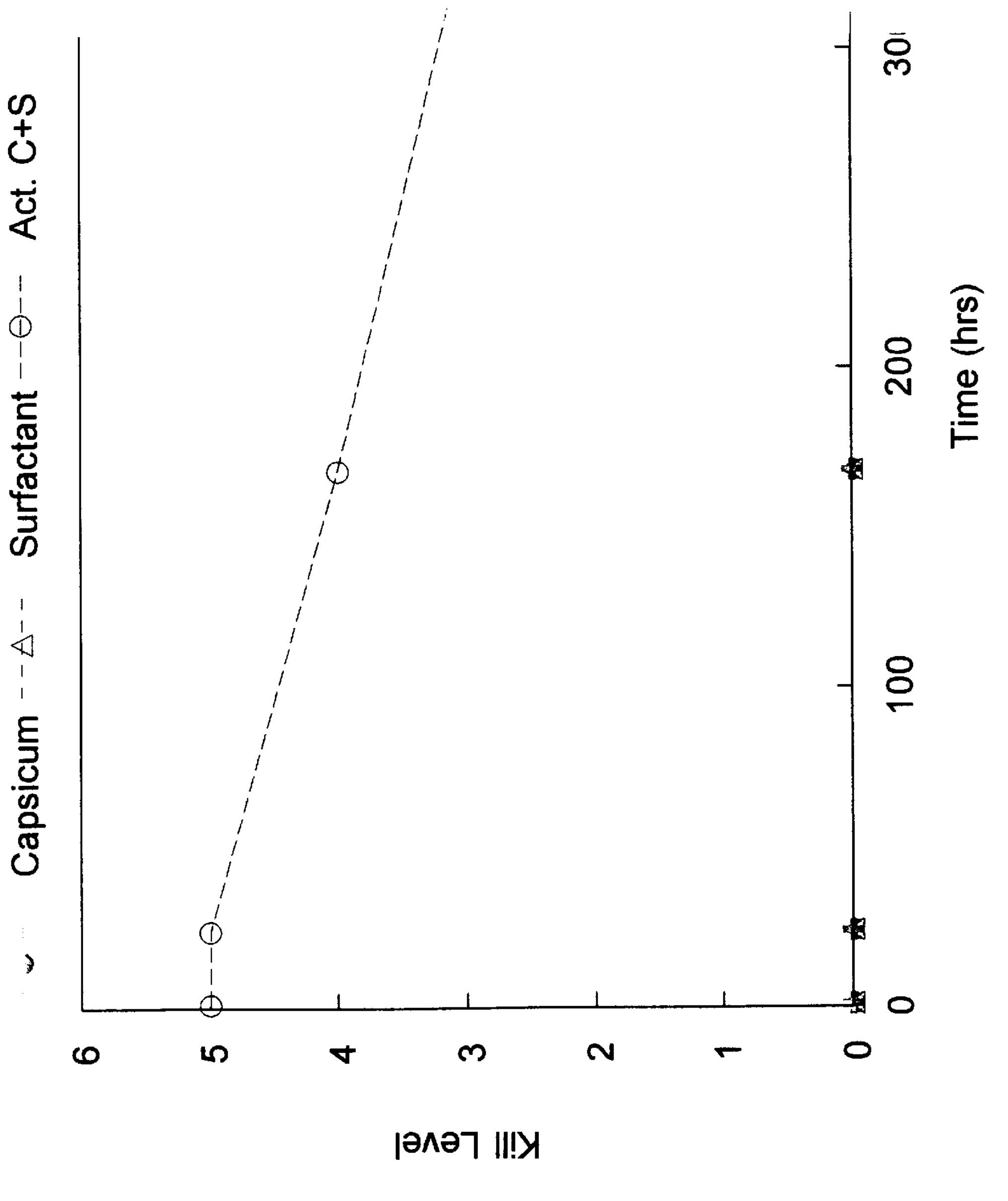

On stage 3 true army worms, the kill level of the combination was unpredictably positive after one hour and after twenty-four hours and was extended out to fourteen days after application as depicted in FIG. 13.

| True Armyworm Time | Kill Levels Stage 3 | | | |
|---|---|---|---|---|
| | Cap-saicinoid | Surfactant | Theoretical Cap-saicinoid + Surfactant | Actual Cap-saicinoid + Surfactant |
| 1 hour | 0 | 0 | 0 | 5 |
| 24 hours | 0 | 0 | 0 | 5 |
| seven days | 0 | 0 | 0 | 4 |
| fourteen days | 0 | 0 | 0 | 3 |

Example 10. Effect on Stage 2 Grasshopper

Figure 14:
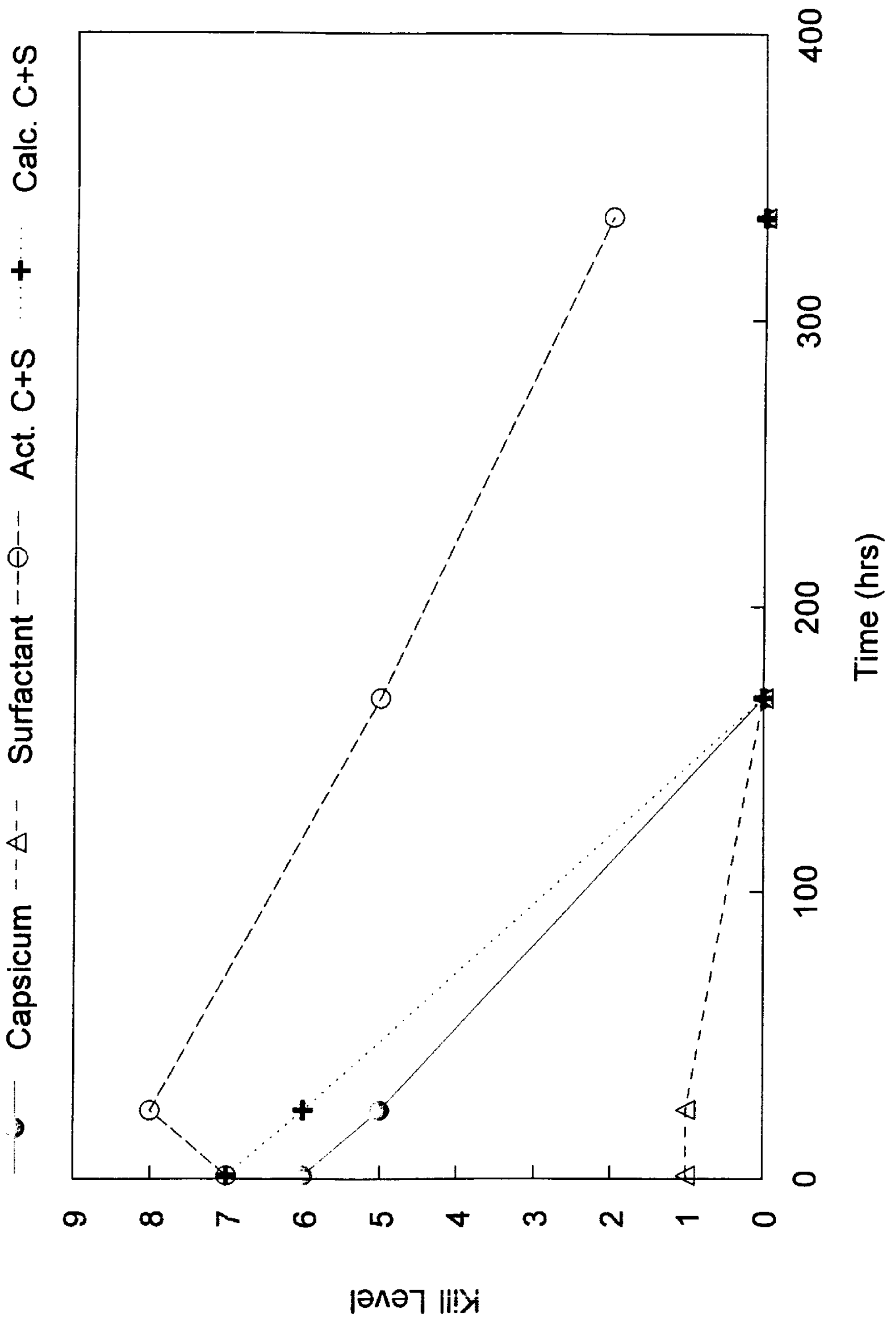

On stage 2 grasshopper, the combination did not exceed the calculated after one hour, only slightly after twenty-four hours, but again was unpredictably extended out to fourteen days after application as depicted in FIG. 14.

| Grasshopper Time | Kill Levels Stage 2 | | | |
|---|---|---|---|---|
| | Cap-saicinoid | Surfactant | Theoretical Cap-saicinoid + Surfactant | Actual Cap-saicinoid + Surfactant |
| 1 hour | 6 | 1 | 7 | 7 |
| 24 hours | 5 | 1 | 6 | 8 |
| seven days | 0 | 0 | 0 | 5 |
| fourteen days | 0 | 0 | 0 | 2 |

Example 11. Showing effect on Corn Flea Beetles in White Corn.

Stands of white corn infested with corn flea beetles are treated separately with an aqueous solution containing 100 ppm capsaicinoids in the form of Capsyn®, an aqueous solution containing 10,000 ppm mixed alkylphenoxy poly (ethyleneoxy) ethanols in the form of Igepal CO 630®, and an aqueous solution containing 100 ppm capsaicinoids plus 10,000 ppm mixed alkylphenoxy poly(ethyleneoxy) ethanols, and are evaluated 72 hours after application. Treatment with the Igepal CO 630® alone leads to a reduction in corn flea beetles of about 5%. Treatment with the capsaicinoid solution alone leads to a reduction of the corn flea beetles of about 50%. Treatment with the combination of 100 ppm capsaicinoids and 10,000 ppm mixed alkylphenoxy poly(ethyleneoxy) ethanols leads to a reduction of the corn flea beetles of about 95%.

Example 12. Showing effect on Fall Army Worms in Field Corn.

Stands of field corn infested with Fall Army Worms are treated separately with an aqueous solution containing 100 ppm capsaicinoids in the form of Capsyn®, an aqueous solution containing 10,000 ppm of Dioctyl Sodium Sulfosuccinate in the form of Pentex 99®, and an aqueous solution containing 100 ppm capsaicinoids plus 10,000 ppm of Dioctyl Sodium Sulfosuccinate, and are evaluated 24 hours after application. Treatment with the insecticidal soap alone leads to a reduction in Fall Army Worms of about 5%. Treatment with the capsaicinoid solution alone leads to a modest reduction in the Fall Army Worms of about 5%. Treatment with the combination of 100 ppm capsaicinoids and 10,000 ppm of Dioctyl Sodium Sulfosuccinate leads to a reduction in the Fall Army Worms of about 50%.

Similar effective compositions contain as the synthetic surfactant dibutyl sodium or potassium sulfosuccinate or di-2-ethylhexyl sodium or potassium sulfosuccinate.

Example 13. Showing effect on Grasshoppers in Soybeans.

Stands of soybeans infested with Grasshoppers are treated separately with an aqueous solution containing 200 ppm capsaicinoids, an aqueous solution containing 10,000 ppm of a mixture of sodium naphthalene sulfonate surfactants in the form of Aerosol OS®, and an aqueous solution containing 200 ppm capsaicinoids plus 10,000 ppm of a mixture of sodium naphthalene sulfonate surfactants, and are evaluated 24 hours after application. Treatment with the surfactant mixture alone leads to a reduction in Grasshoppers of about 0%. Treatment with the capsaicinoid solution alone leads to a reduction in the Grasshoppers of about 5%. Treatment with the combination of 200 ppm capsaicinoids and 10,000 ppm of a mixture of sodium naphthalene sulfonate surfactants leads to a reduction in Grasshoppers of about 40%.

Similar effective compositions contain as synthetic surfactant the potassium salt of naphthalene sulfonic acid or the sodium or potassium salt of diisopropyl naphthalene sulfonic acid.

Example 14. Showing effect on Alfalfa Weevils in a mixed weed, field corn, squash, sunflower, and soybean matrix.

A mixed trap crop consisting of weeds, field corn, squash, sunflower and soybeans infested with Alfalfa Weevils is treated separately with an aqueous solution containing 400 ppm capsaicinoids, an aqueous solution containing 20000 ppm of a mixture of alkyl poly(ethyleneoxy) ethers in the form of Armix 180-C®, and an aqueous solution containing 400 ppm capsaicinoids plus 20000 ppm of a mixture of alkyl poly(ethyleneoxy) ethers, and is evaluated 24 hours after application. Treatment with the surfactant alone leads to a reduction in Alfalfa Weevils of about 5%. Treatment with the capsaicinoid solution alone leads to a reduction of the Alfalfa Weevils of about 10%. Treatment with the combination of 400 ppm capsaicinoids and 20000 ppm alkyl poly(ethyleneoxy) ethers leads to a reduction in the Alfalfa Weevils of about 90%.

Similar effective compositions contain as synthetic surfactant a mixture alkylaryl poly(ethyleneoxy) ethers of the formula

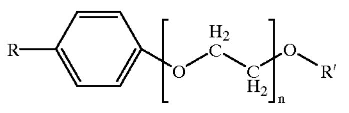

wherein $R=C_4H_9—C_{16}H_{33}$ alkyl, predominantly para oriented, n=4–15, $R'=H$, $CH_3$, or $C_2H_5$.

Discussion

Synthetic surfactants are known to enhance the activity of a number of potent, commercial insecticides. The mechanism may be due to a sheeting action produced by the surface activity. What makes the capsaicinoid/synthetic surfactant activity so surprising is that the capsaicinoid and the synthetic surfactant themselves are relatively ineffective insecticides. We have shown examples where the capsaicinoid or synthetic surfactant applied separately has little to no insecticidal activity. The combination, however, shows enhanced activity and extends it in time far beyond that shown by either constituent alone.

As apparent from the foregoing, the performance parameters of the combination compositions of the present invention exceed the performance parameters of the known ingredients when employed by themselves by an unpredictable activity-enhancing and/or extending amount, so that a synergistic combination is provided by the present invention, especially as to the activity-extending or prolonging aspect, since the individual components are seldom if ever productive of an effective kill rate beyond a period of 24 hours whereas the combination compositions of the present invention produce effective kill rates up to and beyond fourteen (14) days after application.

Although the synergistic activity of the Capsyn® synthetic surfactant combinations (SSC) control programs has been demonstrated, further studies may refine and optimize the schedules required in a particular case for control as indicated by the synthetic surfactant label. By assuring the Pest Management Specialist that better and quicker control is possible with Capsyn®-SSC in the tank-mixture and that, in fact, Capsyn-SSC can be used in place of other less environmentally-friendly insecticides, the result will be a reduced usage of insecticide in the crop production. This reduction of insecticide use should also extend the life of currently-used materials by delaying the development of resistance in the insect populations.

Various Capsyn®-SSC studies are carried out with material applied by aircraft in little water diluent in relation to the active ingredients. No incompatibilities are seen in the concentrated combinations. Thus there should be no problems with more dilute control programs or in ground applications where more water is generally required for distribution of the spray materials. Further studies will determine the optimum concentrations of Capsyn® and surfactant required in the various spray mixtures to obtain the same synergistic effects on various insects.

The versatility and safety of the synergistic insecticidal capabilities of Capsyn®-SSC is also of value in other control programs on many other crops such as potatoes, sweet corn, and other field and vegetable crops. Capsyn®-SSC also have a place in controlling insect pests on ornamentals in the landscape and nursery industries. Capsyn®-SSC can also be used in aerosol sprays for household insect control. Synergized formulations of insecticides are well established for this use.

One main factor in the use of Capsyn® in a spray program is its innate warning to the user of its presence. The resulting sprays containing Capsyn® are extremely noxious and incite coughing in human beings, but are not injurious, thereby making the combinations safer for use than when the capsaicinoid is not present. This safety factor results because protective breathing precautions cannot be forgotten when using the compositions of the present invention, whereas there is often a tendency to neglect protection when normal commercial insecticides are employed.

The use of insecticidal combinations of the present invention containing Capsyn® will be a very important part of Integrated Pest Management (IPM) programs against innumerable economic and regulatory insect species, not only because of its enhanced or prolonged effectiveness after a single application, but also because of its inherently environmentally-friendly character because of the fact that the active ingredients thereof are relatively non-toxic and many possible combinations are readily biodegradable.

It is therefore seen that an improved and highly-advantageous insecticidal composition, suitable for all of its intended purposes and uses, and having a high order of activity enhancement and prolongation in contrast with the same active ingredients when used alone and in any event containing as essential ingredients the synthetic surfactant and the capsaicin and/or other capsaicinoids, as required according to the present invention, is provided by the present invention, with all of its attendant advantages in application or use.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. An insecticidal composition, having enhanced and/or prolonged insecticidal effectiveness when compared with the individual components when used alone, comprising as essential ingredient an effective amount of a combination of (A) at least one synthetic surfactant selected from the group consisting of phosphate esters of alkyl poly(ethyleneoxy) ethanols, phosphate esters of aryl alkyl poly(ethyleneoxy) ethanols, ethers of fatty alcohols and polyethylene glycol, dialkyl sodium or potassium sulfosuccinates, sodium or potassium naphthalene sulfonates, arylalkyl poly (ethyleneoxy) alcohols and ethers, sodium or potassium and potassium alkylarylsulfonates, plus (B) at least one capsaicinoid, the weight ratio of (B) to (A) being between about 1:2.5 and 1:400 and the amount of capsaicinoid to total insecticidal composition, including both active and inactive ingredients, being between about 50 and 2000 parts per million by weight.

2. A composition according to claim 1 wherein the weight ratio of (B) to (A) is between about 1:10 and 1:200.

3. A composition according to claim 1 wherein the weight ratio of (B) to (A) is approximately 1:25 to 1:50 and the amount of capsaicinoid to total insecticidal composition, including both active and inactive ingredients, is between about 100 and 400 parts per million by weight.

4. A composition according to claim 1 wherein the capsaicinoid (B) comprises capsaicin.

5. A composition of claim 1 wherein the capsaicinoid (B) is in the form of an essentially lipid-free and optionally aqueous solution thereof in a polyol.

6. A composition of claim 1 wherein the capsaicinoid (B) is derived from a species of Capsicum.

7. A composition according to claim 6 wherein the capsaicinoid (B) comprises one or more of capsaicin, norcapsaicin, dihydrocapsaicin, nordihydrocapsaicin, homodihydrocapsaicin, and homocapsaicin.

8. A composition of claim 1 wherein the capsaicinoid (B) is a synthetic capsaicinoid.

9. A composition according to claim 8 wherein the capsaicinoid (B) comprises one or more of N-(4-hydroxy-3-methoxybenzyl) heptamide, N-(4-hydroxy-3-methoxybenzyl) octamide, N-(4-hydroxy-3-methoxybenzyl)nonamide, N-(4-hydroxy-3-methoxybenzyl) decamide, N-(4-hydroxy-3-methoxybenzyl) undecamide, and N-(4-hydroxy-3-methoxybenzyl) dodecamide.

10. A composition of claim 1 wherein the synthetic surfactant comprises a mixture of phosphate esters of alkylaryl poly(ethyleneoxy) ethanols of the formula

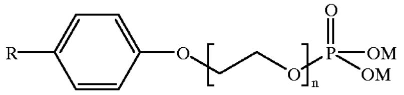

wherein R=$C_4H_9$—$C_{16}H_{33}$ alkyl, predominantly para oriented, n=4–15,

M=H, Na, K, $NH_4$, $CH_3$, or $C_2H$, and phosphate esters of alkyl poly(ethyleneoxy) ethanols of the formula

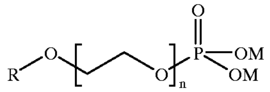

wherein R=$C_4H_9$—$C_{16}H_{33}$ alkyl, n=4–15,

M=H, Na, K, $NH_4$, $CH_3$, or $C_2H_5$.

11. A composition of claim 10 which also contains ammonium and sulfate ions.

12. A composition of claim 1 wherein the synthetic surfactant comprises dibutyl sodium or potassium sulfosuccinate.

13. A composition of claim 1 wherein the synthetic surfactant comprises di-2-ethylhexyl sodium or potassium sulfosuccinate.

14. A composition of claim 1 wherein the synthetic surfactant comprises the sodium or potassium salt of naphthalene sulfonic acid.

15. A composition of claim 1 wherein the synthetic surfactant comprises the sodium or potassium salt diisopropyl naphthalene sulfonic acid.

16. A composition of claim 1 wherein the synthetic surfactant comprises a mixture of alkylaryl poly (ethyleneoxy) ethers of the formula

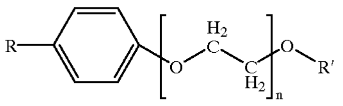

wherein R=$C_4H_9$—$C_{16}H_{33}$ alkyl, predominantly para oriented, n=4–15.

R'=H, $CH_3$, or $C_2H_5$.

17. A composition of claim 1 in the form of a dilutable concentrate.

18. A concentrate of claim 17 wherein the composition is dilutable with water.

19. A composition of claim 1 wherein (B) is capsaicin or a mixture of capsaicinoids and (A) comprises a mixture of phosphate esters of alkylaryl poly(ethyleneoxy) ethanols of the formula

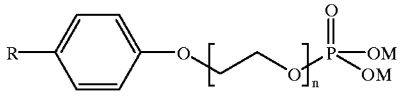

wherein $R=C_4H_9—C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

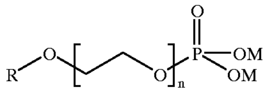

wherein $R=C_4H_9—C_{16}H_{33}$ alkyl, n=4-15,

M=H, Na, K, $NH_4$, $CH_3$, or $C_2H_5$.

20. A composition of claim 1 wherein the synthetic surfactant is selected from the group consisting of sulfosuccinates, naphthalene sulfonates, alkyl poly (ethyleneoxy) ethers, and alkylaryl poly(ethyleneoxy) ethanols.

21. A method of killing insects comprising the step of spraying a combination of (A) at least one synthetic surfactant as defined in claim 1 plus (B) at leat one capsaicinoid, upon the insect or upon its habitat, the weight ratio of (B) to (A) being between about 1:2.5 and 1:406 and the amount of capsaicinoid to total insecticidal composition, including both active and inactive ingredients, being between about 50 and 2000 parts per million by weight.

22. A method of claim 21 wherein the capsaicinoid (B) is in the form of an essentially lipid-free and optionally aqueous solution thereof in a polyol.

23. A method of claim 21, wherein (B) comprises at least one capsaicinoid and (A) comprises a mixture of phosphate esters of alkylaryl poly(ethyleneoxy) ethanols of the formula

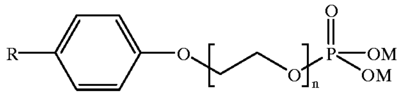

wherein $R=C_4H_9—C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

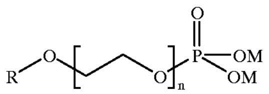

wherein $R=C_4H_9—C_{16}H_{33}$ alkyl, n=4–15,

M=H, Na, K, $NH_4$, $CH_3$, or $C_2H_5$.

24. A method for controlling insects comprising contacting insects or their habitat with an insecticidally-active composition of claim 2.

25. A method of claim 24, wherein (B) is at least one capsaicinoid and (A) comprises a mixture of phosphate esters of alkylaryl poly(ethyleneoxy) ethanols of the formula

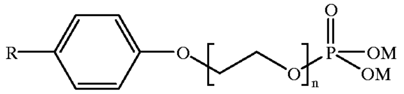

wherein $R=C_4H_9—C_{16}H_{33}$ alkyl, predominantly para oriented, n=4–15,

M=H, Na, K, $NH_4$, $CH_3$, or $C_2H_5$, and phosphate esters of alkyl poly(ethyleneoxy) ethanols of the formula

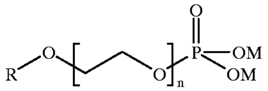

wherein $R=C_4H_9—C_{16}H_{33}$ alkyl, n=4–15,

M=H, Na, K, $NH_4$, $CH_3$, or $C_2H_5$.

26. A method of controlling insects which comprises applying, to the insects or their habitat, an insecticidally-effective amount of a composition of claim 3.

27. A method of claim 25 wherein the concentration of capsaicinoids plus synthetic surfactant in the composition is between about 1050 and 22,000 ppm by weight.

28. A method of controlling insects which comprises applying, to the insects or their habitat, an insecticidally-effective amount of a composition of claim 1.

29. A method of claim 28 wherein the concentration of capsaicinoids plus synthetic surfactant in the composition is between about 1050 and 22,000 ppm by weight.

30. A method of claim 28 wherein the habitat is living plants.

31. A method of claim 30 wherein the plants are grasses, beans, corn, garden vegetables fruits, or flowers.

32. A method of claim 30 wherein the plants are field corn, soybeans, sunflowers, or squash plants.

33. A method of claim 30 wherein the composition is applied by spraying.

34. A method of claim 33 wherein the composition is applied by aerial spraying.

35. A method of claim 28 wherein the weight ratio of (B) to (A) is between about 1:2.5 and 1:50 by weight.

36. A method according to claim 28 wherein active ingredients are applied at a rate of about 0.17 to about 7.2 pounds per acre.

37. A method of claim 28 wherein the total composition is applied at a rate of about 24 to about 500 pounds per acre.

38. A method of claim 28, wherein the total composition is applied at a rate of about 80 to about 320 pounds per acre.

39. A method of claim 28 wherein the concentration of active ingredients is about 0.1 to 2.2 percent by weight of the total composition.

40. A method of claim 28, wherein the insect controlled is selected from the group consisting of Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips.

41. A method of claim 28 wherein (B) is oleoresin capsicum.

42. A method of claim 28, wherein the insect controlled is selected from the group consisting of Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips and the habitat protected is a plant selected from the group consisting of grasses, beans, corn, garden vegetables, fruits, and flowers.

43. A method of controlling insects which comprises applying, to the insects or their habitat, an insecticidally-effective amount of a composition of claim 19.

44. A method of controlling insects which comprises applying, to the insects or their habitat, an insecticidally-effective amount of a composition of claim 20.

45. A method of enhancing the insecticidal activity of (A) a synthetic surfactant composition the surfactant being defined as in claim 1, comprising the step of including in said composition an effective insecticidal-activity-enhancing amount of (B) at least one capsaicinoid, the weight ratio of capsaicinoid to synthetic surfactant being between about 1:2.5 and 1:400 and the amount of capsaicinoid to total insecticidal composition, including both active and inactive ingredients, being between about 50 and 2000 parts per million by weight.

46. A method of claim 45 wherein the weight ratio is between about 1:25 and about 1:50 and the amount of capsaicinoid to total insecticidal composition, including both active and inactive ingredients, is between about 100 and 400 parts per million by weight.

47. A method of claim 45 wherein the capsaicinoid comprises capsaicin.

48. A method of claim 47, wherein the capsaicin is in the form of an essentially lipid-free and optionally aqueous solution thereof in a polyol.

49. A method of claim 45, wherein (B) is at least one of capsaicin, norcapsaicin, dihydrocapsaicin, nordihydrocapsaicin, homodihydrocapsaicin, homocapsaicin, N-(4-hydroxy-3-methoxybenzyl) heptamide, N-(4-hydroxy-3-methoxybenzyl) octamide, N-(4-hydroxy-3-methoxybenzyl) nonamide, N-(4-hydroxy-3-methoxybenzyl) decamide, N-(4-hydroxy-3-methoxybenzyl) undecamide, and N-(4-hydroxy-3-methoxybenzyl) dodecamide.

50. A method of claim 49, wherein the capsaicinoid is in the form of an essentially lipid-free and optionally aqueous solution thereof in polyol.

51. A method of claim 49, wherein the enhancement relates to the protection of a plant selected from the group consisting of grasses, beans, corn, garden vegetables, fruits, and flowers against an insect selected from the group consisting of Fall Army Worms, Alfalfa Weevils, Corn Ear Worms, Corn Leaf Aphids, True Army Worms, Grasshoppers, Potato Leaf Hoppers, Beanleaf Beetles, Corn Flea Beetles, Stink Bugs, European Corn Borer, and Soybean Thrips.

52. A method of claim 49, wherein (B) comprises at least one capsaicinoid and (A) comprises a mixture of phosphate esters of alkylaryl poly(ethyleneoxy) ethanols of the formula

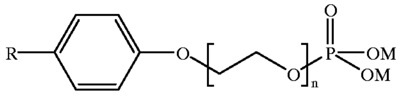

wherein R=$C_4H_9$—$C_{16}H_{33}$alkyl, predominantly para oriented, n=4–15,

M=H, Na, K, $NH_4$, $CH_3$, or $C_2H_5$, p1 and phosphate esters of alkyl poly(ethyleneoxy) ethanols of the formula

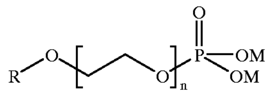

wherein R=$C_4H_9$—$C_{16}H_{33}$ alkyl, n=4–15,

M=H, Na, K, $NH_4$, $CH_3$, or $C_2H_5$.

* * * * *

UNITED STATES PATENT AND TRADEMARK OFFICE

CERTIFICATE OF CORRECTION

PATENT NO. : 6,069,173

DATED : May 30, 2000

INVENTOR(S) : Gary C. Hainrihar

It is certified that error appears in the above-indentified patent and that said Letters Patent is hereby corrected as shown below:

Column 1, line 65: "atents" should read: -- patents --. Page 2, line 36

Column 1, line 66: "ust" should read: -- just --. Page 2, line 37

Column 3, line 24: "Capslcum;" should read: -- Capsicum; --. Page 5, line 16

Column 3, line 39: "(eyleneoxy)" should read: -- (ethyleneoxy) --. Page 5, line 31

Column 10, line 9: "(diatomalesus" should read: -- (diatomaceous --. Response and Amendment dtd 8/17/99, SPECIFICATION, page 17, line 21.

Column 10, line 20: "capsaicinbid" should read: -- capsaicinoid --. Page 17, line 32

Column 19, lines 39 and 40: "sodium or potassium an potassium" should read: -- and sodium or potassium --. Response and Amendment dtd 12/13/99, Claim 1, line 14.

UNITED STATES PATENT AND TRADEMARK OFFICE

CERTIFICATE OF CORRECTION

PATENT NO. : 6,069,173

DATED : May 30, 2000

INVENTOR(S) : Gary C. Hainrihar

It is certified that error appears in the above-indentified patent and that said Letters Patent is hereby corrected as shown below:

Column 21, line 33: "leat" should read: -- least --.
Page 39, line 3

Column 21, line 35: "1:406" should read -- 1.400 --.
Page 39, line 5

Column 24, line 30: Delete "p1". Page 44, line 14

Signed and Sealed this

Twenty-fourth Day of April, 2001

Attest:

NICHOLAS P. GODICI

Attesting Officer

*Acting Director of the United States Patent and Trademark Office*